United States Patent
Smith et al.

(10) Patent No.: US 7,230,015 B2
(45) Date of Patent: Jun. 12, 2007

(54) METHOD OF TREATING OF DEMYELINATING DISEASES OR CONDITIONS

(75) Inventors: Craig P Smith, Hillsborough, NJ (US); Michel P Rathbone, Hamilton, CA (US); Margaret Petty, Bridgewater, NJ (US); David Rampe, Bernardsville, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 30 days.

(21) Appl. No.: 11/079,327

(22) Filed: Mar. 14, 2005

(65) Prior Publication Data

US 2005/0159456 A1     Jul. 21, 2005

Related U.S. Application Data

(60) Continuation of application No. 10/770,655, filed on Feb. 3, 2004, now abandoned, which is a division of application No. 10/076,191, filed on Feb. 14, 2002, now Pat. No. 6,967,210.

(60) Provisional application No. 60/268,846, filed on Feb. 15, 2001.

(30) Foreign Application Priority Data

Aug. 9, 2001    (GB)    ................... 0119435.6

(51) Int. Cl.
A61K 31/44    (2006.01)

(52) U.S. Cl. .............. 514/339; 514/323; 514/336; 514/337; 514/903

(58) Field of Classification Search .............. None
See application file for complete search history.

(56) References Cited

U.S. PATENT DOCUMENTS 4,970,218 A    11/1990    Effland et al.
5,519,131 A    5/1996    Effland et al.

FOREIGN PATENT DOCUMENTS

| DE | 43 25 491 | 2/1995 |
| EP | 0287982 | 12/1994 |
| EP | 0415103 | 2/1995 |
| EP | 0731108 | 9/1996 |
| EP | 0683165 | 8/2000 |
| WO | WO 96/14066 | 5/1996 |
| WO | WO 01/04091 | 1/2001 |

OTHER PUBLICATIONS

Bever, C.T., et. al., The Current Status of Studies of Aminopyrides in Patients with Multiple Sclerosis, Annals of Neurology, Boston, MA, vol. 36, 1994, pp. S118-S121.
Tang, L., et. al., 4-Aminopyridine Derivatives: A Family of Novel Modulators of Voltage-Dependent Sodium Channels, Drug Development Research, vol. 44, No. 1, May 1998, pp. 8-13.
Tang, L., et. al., Effects of besipirdine at the voltage-dependent sodium channel, British Journal of Pharmacology, vol. 116, No. 5, 1995, pp. 2468-2472.
Abou-Gharbia, M., et. al., IV Congress of the ECNP, Aggression and anxiety are the first components to respond to antidepressant therapy, Drug News and Perspectives, vol. 4, No. 10, Dec. 1, 1991, pp. 647-650.
Villoslada, P., et. al., Human Nerve Growth Factor Protects Common Marmosets against Autoimmune Encephalomyelitis by Switching the Balance of T Helper Cell Type 1 and 2 Cytokines within the Central Nervous System, Journ. of Experimental Medicine, vol. 191, No. 10, May 15, 2000, pp. 1799-1806.
Eglen, R.M., et. al., Muscarinc receptor ligands and their therapeutic potential, Current Opinion in Chemical Biology, vol. 3, No. 4, Aug. 1999, pp. 426-432.
Stedman's, No title—Stedman's Medical Dictionary, Stedman's Medical Dictionary, 25th Edition, Illustrated, 1994, pp. 391.
Mysiw, M.J., et. al., Medications To Enhance Cognitive Functioning, Physical Medicine and Rehabilitation Clinics of North America, 1997, pp. 781-800.

*Primary Examiner*—Dwayne Jones
(74) *Attorney, Agent, or Firm*—Barbara E. Kurys

(57) ABSTRACT

N-(Pyridinyl)-1H-indol-1-amines of formula I provide a unique combination of blocking properties for both the potassium and sodium channels. These compounds are useful for the treatment of Demyelinating Diseases and Conditions such as Multiple Sclerosis, Spinal Cord Injury, Traumatic Brain Injury and Stroke. The compounds are also useful for Stroke Rehabilitation, the treatment of Bladder Irritation and Dysfunction, and the treatment of Neuropathic Pain and Chemokine-Induced Pain.

2 Claims, 11 Drawing Sheets

METHOD OF TREATING OF DEMYELINATING DISEASES OR CONDITIONS

CROSS REFERENCE TO RELATED APPLICATIONS

This application is a continuation of U.S. application Ser. No. 10/770,655 filed Feb. 3, 2004, now abandoned which is a divisional of U.S. application Ser. No. 10/076,191 filed on Feb. 14. 2002, now U.S. Pat. No. 6,967,210 which claims the benefit of U.S. Provisional Application No. 60/268,846, filed Feb. 15, 2001, and claims priority to GB 0119435.6, filed Aug. 9, 2001, which are hereby incorporated by reference herein in their entireties.

BACKGROUND OF THE INVENTION

Multiple sclerosis (MS) is a degenerative and inflammatory neurological disease that affects the central nervous system, and is associated with formation of neuronal plaques and impaired neuronal conduction due to demyelination (loss of myelin). Similarly, extensive demyelination is commonly reported in spinal cord trauma and stroke (Bunge et al, 1993; Blight and DeCrescito, 1986; Pendlebury et al, 2000).

Basic research into the physiology of the action potential propagation in myelinated fibers showed that conduction block in demyelinated fibers was partly due to the appearance of aminopyridine-sensitive potassium channels in areas of myelin loss (Bever 1996).

Action potentials propagate along normal myelinated nerve fibers by a process of salutatory conduction, which results from a sodium current generated by the opening of voltage-sensitive sodium channels at the node of Ranvier. Thus, at the onset of electrical stimulation, sodium ($Na^+$) ions enter the neuron, causing the neuron to become more positively charged. When the positive nature of the neuron approaches a critical level, "depolarization" occurs. Depolarization allows a positive core of ions to flow down the neuron, along the axon and to the nerve ending. For the neuron to "reset" itself, the excess positive charge must be dissipated. This is done via the outflow of potassium ions (hereinafter "$K^+$") through potassium channels. When myelin is disrupted, voltage-sensitive potassium channels that open during depolarization appear on the axolemma. The potassium current, flowing opposite to the sodium current, decreases action potential amplitude and duration, contributing to conduction failure by decreasing the distal effective current densities. These conduction deficits are associated with disabling symptoms, including muscle weakness. By blocking the outflow of $K^+$ through potassium channels, the neuron remains depolarized longer and is more easily restimulated. Thus, potassium channel blockers are believed to be useful in the treatment of diseases and conditions which impair action potential transmission such as MS, Traumatic Brain Injury (hereinafter "TBI") and Spinal Cord Injury (hereinafter "SCI").

Potassium channel blockers, such as 4-amino pyridine (hereinafter "4-AP"), increase action potential duration and amplitude in demyelinated fibers and improve action potential propagation in vitro (Bostock et al, 1978; 1981; Targ and Kocsis, 1985; 1986; Shi and Blight, 1997), facilitate neurotransmitter release (Bostock et al, 1981; Hirsh and Quandt, 1993; Sherratt et al, 1980), and potentiate muscle contractility (Agoston et al, 1982; Savage et al, 1985). These observations suggested that potassium channel blockers, such as 4-AP, could restore conduction in demyelinated fibers in MS patients. Subsequent clinical trial results lend further support the proposition that aminopyridine treatment may improve symptoms in some MS patients (Jones et al 1983; Stefoski et al, 1987; Davis et al, 1990; van Diemen et al, 1992; Bever et al, 1994; Schwid et al, 1997).

4-AP has also been disclosed to be effective in the treatment of neurological conditions including SCI, reduction of chronic pain and spasticity in SCI patients, Alzheimer's disease, post-polio syndrome, myasthenia gravis, Huntington's disease, age-related memory disorders, post-traumatic, post-stroke or post-toxic syndromes affecting memory or cognition, and dysautonomia (Wurtman R J and Buyukuysal R, 1989; Hansebout R R and Blight A, 1996; Hansebout R R and Blight A 1994). Clinical studies for the use of Fampridine-SR in long-term spinal cord injured patients have begun (Potter et al, 1998a,b) notwithstanding safety concerns surrounding use of 4-AP in the general patient population (Multiple Sclerosis, Cognos Study #51, Decisions Resources, October, 1999; pp 77–8). Several studies have shown that single doses of 4-AP can restore some function in SCI patients when administered one year or longer after injury (Potter et al, 1998a,b; Oiao et al, 1997; Hayes et al, 1993; 1994). Positive effects after chronic dosing have also been reported. Clinically significant functional improvements were observed in 16 out of 16 patients after 3 months of daily oral dosing with 30 mg/kg 4-AP in patients with SCI of 2 years or more. Some patients previously classified as having complete injury were reclassified to incomplete injury level (Segal et al, 1999). All patients showed some degree of improvement in at least some type of neurolgic or pulmonary function after 3 months of daily oral treatment with 4-AP (30 mg/day, or approximately 0.5 mg/kg). A lower dose was not active.

As previously stated, 4-AP blocks potassium channels, effectively prolonging the action potential. Unfortunately, this mechanism by which potassium channel blockers can improve symptoms associated with diseases and conditions which impair action potential transmission can also lead to epileptic-like activity. Indeed, 4-AP is a recognized convulsive agent in animals and humans. Therefore, the usefulness of 4-AP as a therapeutic agent for MS, TBI and SCI is tempered by its pro-convulsant liability and other undesirable side effects. Restlessness, confusion, and generalized tonic-clonic seizures have been reported at doses higher than 0.8 mg/kg (Ball et al, 1979; Bever et al, 1994). Van Diemen et al (1993) reported that magnitude of improvement in MS patients (defined by improvement in smooth pursuit gain) was significantly related to 4-AP serum level, (33–75 ng/ml necessary for significant improvement after oral administration). However, side effects (paresthesia/dysestheia, dizziness/light-headedness, and even gait instability) were observed at the same doses. In another human study, Bever et al (1994) reported a grand mal seizure at a serum level of 104 ng/ml. Both groups of investigators suggested that higher dosages and serum levels would be likely to produce greater improvements in those MS patients which responded to lower doses of 4-AP. Thus, the degree of efficacy with 4-AP is dose- and side effect-limited.

Concern about the side-effects associated with higher 4-AP serum levels has led to the development of sustained release formulations (Fampridine-SR) (Masterson J G and Myers M, 1994; 1996a; 1996b). Fampridine-SR is currently in Phase 2 clinical studies for MS. Patients in prior clinical studies of Fampridine-SR have shown improvement in a variety of functions. Depending on the individual, these improvements have included enhanced bladder, bowel, and sexual function, increased ease of movement and sensation, and reduced muscle spasticity, fatigue and chronic pain.

Another approach to eliminating the undesirable side effects associated with 4-AP involves coadministration of 4-AP and voltage dependent sodium channel blockers. Sodium ($Na^+$) channel blockers block the inflow of $Na^+$ ions and reduce the susceptibility of the neuron to depolarization. This effectively reduces neuronal excitability. Indeed, it has been reported that coadministration of voltage-dependent sodium channel blockers and 4-AP prevents 4-AP-induced convulsions in mice (Yamaguchi and Rogawski, 1992). 4-AP has no sodium channel blocking properties.

The compounds used in the methods claimed herein can be synthesized via procedures disclosed in U.S. Pat. No. 4,970,218. All patents and other publications cited herein are hereby incorporated by reference.

It is known that certain compounds within the scope of the present invention can induce voltage-dependent blockade of sodium channels in vitro and in vivo (Tang et al, 1995; 1998; Tang and Kongsamut, 1996). Voltage-dependent sodium channel blockers act more effectively during conditions of cellular depolarization. These compounds have little or no effect on normal neuronal signaling, but allow the blockade of sodium channels during seizures, head trauma or ischemia. Many of these agents are cerebroprotective in animal models of these pathological conditions (Madge et al, 1998).

Without wishing to be bound by theory, potassium channel blockers are also viable agents for the treatment of neuropathic pain and cytokine-related pain, including arthritic pain. Sweitzer et al (1999) has suggested that microglial activation and cytokine release may play a role in the hyperalgesia following either peripheral inflammation or peripheral nerve injury. Potassium channel blockers, such as 4-AP, have been reported to block the activation of rat, mouse and human microglia (Eder, 1998). Pyo et al (1997) have reported that 4-AP can reduce nitrite release from activated microglia, indicating that pain behaviors can be regulated via this mechanism. In addition, 4-AP has been reported to reduce lipopolysaccahride (LPS)-induced NO production from murine macrophages (Lowry et al, 1998). The administration of LPS to mice has also been used as a model system for the identification of anti-arthritic efficacy with several different agents with different mechanisms of action (McIlay et al, 2001). Several experimental models which involve constriction of the sciatic nerve or the L5 or L6 spinal nerve have been developed to explore neuropathic pain (Bennett and Xie, 1988; Seltzer et al, 1990; Kim and Chung, 1992).

SUMMARY OF THE INVENTION

It has now been discovered that compounds of formula I possess potassium channel blocking properties. The unique combination of blocking properties for both the potassium and sodium channels means that these compounds are useful as therapeutic agents for the treatment of demyelinating diseases or conditions. For example, they are useful in treating MS, SCI, TBI (traumatic brain injury) and stroke. These compounds provide for a safer therapeutic agent than 4-AP because 4-AP only blocks the potassium channel which can lead to the undesirable side effects of restlessness, confusion, and seizures. The compounds of formula I are also useful for stroke rehabilitation, the treatment of bladder irritation and dysfunction, the treatment of visceral, chemokine-induced pain (including arthritic pain) and neuropathic pain.

BRIEF DESCRIPTION OF THE SEVERAL VIEWS OF THE DRAWING(S)

DETAILED DESCRIPTION OF THE INVENTION

Figure 1:
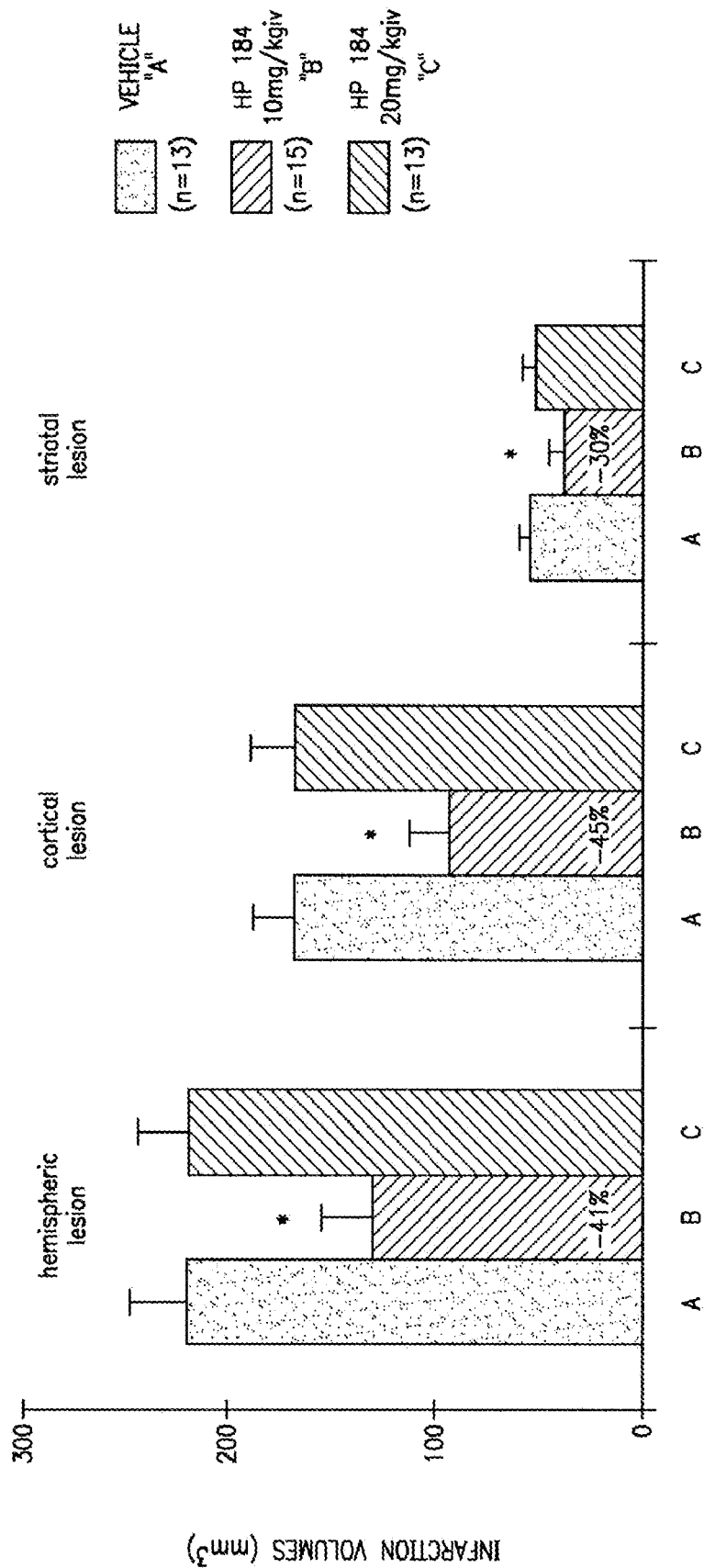
FIG. 1 illustrates the effect of HP184 on brain damage at 10 and 20 mg/kg iv bolus 1 hour after MCA Occlusion—(Example Three).

The compounds of formula I provide a unique combination of blocking properties for both the potassium and sodium channels. These compounds are useful for the treatment of Demyelinating Diseases and Conditions such as Multiple Sclerosis, Spinal Cord Injury, Traumatic Brain Injury and Stroke. The compounds are also useful for Stroke Rehabilitation, the treatment of bladder irritation and dysfunction, the treatment of visceral, chemokine-induced pain (including arthritic pain) and neuropathic pain.

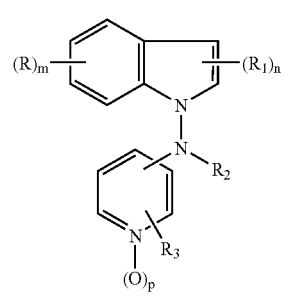

wherein
m is 0, 1 or 2;
n is 0, 1 or 2;
p is 0 or 1;
each R is independently hydrogen, halogen, trifluoromethyl, $C_1$–$C_6$alkyl, $C_1$–$C_6$alkoxy, benzyloxy, hydroxy, nitro or amino;

each $R_1$ is independently hydrogen, $C_1$–$C_6$alkyl, $C_1$–$C_6$alkenyl, $C_1$–$C_6$alkanoyl, halogen, cyano, —C(O)$C_1$–$C_6$alkyl, —$C_1$–$C_6$alkyleneCN, —$C_1$–$C_6$alkyleneNR'R" wherein R' and R" are each independently hydrogen or $C_1$–$C_6$alkyl, —$C_1$–$C_6$alkyleneOC(O)$C_1$–$C_6$alkyl, or —CH(OH)$R_4$ wherein $R_4$ is hydrogen or $C_1$–$C_6$alkyl;

$R_2$ is hydrogen, $C_1$–$C_6$alkyl optionally substituted with halogen, hydroxy or benzyloxy, $C_1$–$C_6$alkenyl, $C_1$–$C_6$alkynyl, —CO$_2$$C_1$–$C_6$alkyl, or —$R_5$—NR' R" wherein $R_5$ is $C_1$–$C_6$alkylene, $C_1$–$C_6$alkenylene or $C_1$–$C_6$alkynylene and R' and R" are each independently hydrogen, $C_1$–$C_6$alkyl or alternatively the group —NR'R" as a whole is 1-pyrrolidinyl; and $R_3$ is hydrogen, nitro, amino, halogen, $C_1$–$C_6$alkoxy, hydroxy or $C_1$–$C_6$alkyl.

Definitions:

1) Demyelinating Diseases: As used herein, Demyelinating Diseases are defined as those diseases in which myelin is the primary target. They fall into two main groups: acquired diseases and hereditary metabolic disorders.

Multiple sclerosis (MS) falls under the category of acquired disease. MS usually manifests itself between the 20th and 50th years of life. MS attacks the white matter of the central nervous system. In its classic manifestation (90% of all cases), it is characterized by alternating relapsing/remitting phases—with periods of remission growing shorter over time. Its symptoms include any combination of spastic paraparesis, unsteady gait, diplopia, and incontinence.

The category of Hereditary Metabolic Disorders includes the eight identified leukodystrophies: metachromatic leukodystrophy, Refsum's disease, adrenoleukodystrophy, Krabbe's disease, phenylketonuria, Canavan disease, Pelizaeus-Merzbacher disease and Alexander's disease. The first six are storage disorders. The lack or the malfunctioning of an enzyme causes a toxic buildup of chemical substances. The etiology of Pelizaeus-Merzbacher and Alexander's diseases, on the other hand, remains unknown.

The clinical course of hereditary demyelinating disorders, which usually tend to manifest themselves in infancy or early childhood, is tragic. Previously normal children are deprived, in rapid progression, of sight, hearing, speech, and ambulation. The prognosis is death within a few years.

2) Demyelinating Conditions—As defined herein, a Demyelinating Condition is a condition that results in deficient myelination. Such demyelinating conditions include, but are not limited to, spinal cord injury, traumatic brain injury and stroke.

3) Spinal Cord Injury (SCI)—As used herein, SCI is defined as an injury to the spinal cord that results in loss of function such as mobility or feeling.

4) Traumatic Brain Injury (TBI)—As used herein, traumatic brain injury is defined as an injury that results in damage to the brain. Head injury may occur in one of two ways:

A closed head injury occurs when the moving head is rapidly stopped, as when hitting a windshield, or when it is hit by a blunt object causing the brain to smash into the hard bony surface inside the skull. Closed head injury may also occur without direct external trauma to the head if the brain undergoes a rapid forward or backward movement, such as when a person experiences whiplash.

A penetrating head injury occurs when a fast moving object such as a bullet pierces the skull.

Both closed and penetrating head injuries may result in localized and widespread, or diffuse, damage to the brain. The resulting disabilities can include memory loss and emotional disturbance, motor difficulties, including paralysis, and damage to the five senses. In addition, many patients die from their injuries.

Today, treatment focuses on containing as much damage as possible in the 24-hour period following the injury. When someone suffers an injury to the brain, the resulting devastation extends beyond the initial trauma. A cascade of "secondary damage" ensues. The brain's own immune cells trigger swelling and fluid buildup, and the injured nerve cells begin to spill out the neurotransmitter called glutamate, which can soon accumulate to levels that are toxic to the surrounding neurons.

5) Stroke rehabilitation—As used herein, stroke rehabilitation is defined as intervention that results in the recovery functions that have been lost due to stroke.

6) Stroke—As defined herein, a stroke occurs when a blood clot blocks a blood vessel or artery, or when a blood vessel breaks, interrupting blood flow to an area of the brain. When a stroke occurs, it kills brain cells in the immediate area. Doctors call this area of dead cells an infarct. These cells usually die within minutes to a few hours after the stroke starts. In stroke, measures of demyelination such as magnetisation transfer ratio (MTR) are closely related to axonal damage which correlates to motor deficit (Pendlebury et al, 2000).

7) Alkyl or alkylene—Unless otherwise stated or indicated, the term "Alkyl" or "alkylene" means a branched or straight chain alkyl or alkylene group, as is appropriate to the formula, specified by the amount of carbons in the alkyl, e.g., $C_1$–$C_6$ alkyl means a one, two, three, four, five or six carbon branched or straight chain alkyl or alkylene, as the case may be, or any ranges thereof, for example, but not limited to, C1–2, C1–3, C1–4, C1–5, C2–3, C2–4, C2–5, C2–C6, C3–C4, C3–5, C3–6, C4–5, C4–6, C5–6, etc.

8) $C_1$–$C_6$alkoxy—Unless otherwise stated or indicated, the term $C_1$–$C_6$alkoxy denotes a straight or branched alkoxy group having from 1 to 6 carbon atoms. Examples of said include methoxy, ethoxy, n-proxy, isopropoxy, n-butoxy, iso-butoxy, sec-butoxy, t-butoxy and straight-and branched-chain pentoxy and hexoxy.

9) Halogen—Unless otherwise stated or indicated, the term halogen shall mean fluorine, chlorine, bromine or iodine.

10) $C_1$–$C_6$alkanoic acid—Unless otherwise stated or indicated, the term $C_1$–$C_6$alkanoic acid shall mean a carboxylic acid in which the carboxyl group is attached to hydrogen or an alkyl group of from 1 to 5 carbon atoms.

11) $C_1$–$C_6$alkanoyl—The term $C_1$–$C_6$alkanoyl shall mean a group obtained by removing a hydroxy group from the carboxyl group of a $C_1$–$C_6$alkanoic acid, and thus it includes for instance formyl, acetyl and the like. The terms alkanoyl, alkenoyl and alkynoyl shall mean groups obtained by removing a hydroxy group from the carboxyl group of alkanoic acid, alkenoic acid and alkynoic acid, respectively. Thus, for instance, linoleyl group derived from linoleic acid is an example of the term alkenoyl as defined above.

12) "Pharmaceutically acceptable salts" means either an acid addition salt or a basic addition salt which is compatible with the treatment of patients for the intended use.

13) "Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids.

Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

14) "Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

15) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

16) "Patient" means a warm blooded animal, such as for example rat, mice, dogs, cats, guinea pigs, and primates such as humans.

17) "Treat" or "treating" means to alleviate symptoms, eliminate the causation of the symptoms either on a temporary or permanent basis, or to prevent or slow the appearance of symptoms of the named disorder or condition.

18) "Therapeutically effective amount" means a quantity of the compound which is effective in treating the named disorder, disease or condition.

19) "Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

20) "Neuropathic Pain" means pain that results from damage to the nervous system. The nerve damage may be identified or unidentified. Examples of Neuropathic Pain include post-herpetic neuralgia, painful diabetic neuropathy, phantom limb pain and central post-stroke pain.

21) "Bladder Irritation and Dysfunction" means conditions such as interstial cystitis and over-active bladder. Overactive bladder is a distinct medical condition characterized by symptoms including urinary frequency, urgency, and urge incontinence, the accidental loss of urine that occurs after the strong sudden urge to urinate. Diagnosis of overactive bladder is made in the absence of local pathological or metabolic-related etiologies, with symptoms attributable to involuntary bladder contractions due to over-activity of the detrusor muscle. Interstial Cystitus (IC) is a chronic inflammatory condition of the bladder wall, which frequently goes undiagnosed.

The compounds of formula I can effectively improve rate and degree of recovery in acute spinal cord injury and long-standing spinal cord injury. They have properties consistent with use-dependent sodium channel blockade and voltage-dependent potassium channel blockade in vivo. They provide a safer therapeutic than 4-AP. Particularly preferred are compounds wherein R is hydrogen, halogen, trifluoromethyl, or $C_1$–$C_6$alkyl; $R_1$ is hydrogen or $C_1$–$C_6$alkyl; $R_2$ is hydrogen or $C_1$–$C_6$alkyl; $R_3$ is hydrogen, $C_1$–$C_6$alkyl or halogen; and p is 0. Further preferred compounds are those wherein the amino group is attached to the 4-position of the pyridine group.

Even more particularly preferred are the compounds of formulas II [also known herein as HP184 or N-(3-fluoro-4-pyridinyl)-N-propyl-3-methyl-1H-indole-1-amine] and III (also known herein as "8183").

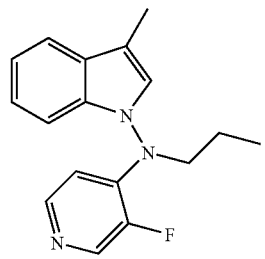

II

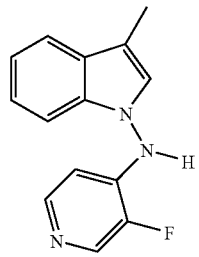

III

HP184 is very well-tolerated in micromolar brain concentrations one hour after ip administration of 30 mg/kg HP 184 in rats (Smith et al, 1996).

The unique combination of use-dependent sodium channel blockade and voltage-dependent potassium channel blockade also differentiates the compounds of the instant invention from "pure" sodium channel blockers such as carbamazepine and phenyloin. These agents have been successfully used to alleviate "positive" symptoms of MS (painful tonic seizure and dysesthesia). However, they worsen negative symptoms (paralysis and hypesthesia) (Sakurai and Kanazawa, 1999). Compounds of the instant invention enhance neuronal function due to the fact that they block the potassium channels. This aids in functional recovery. At present, sodium channel blockers are believed useful useful in the treatment of painful symptoms and/or as neuroprotective agents. They would not, however, be expected to enhance rehabilitative efforts.

In treating a patient afflicted with a condition or disorder described above, a compound of formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of the present invention may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula (I) of this invention may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The highly lipophilic esters, amides and carbamates of the present invention are capable of sustained release in mammals for a period of several days or from about one to four weeks when formulated and administered as depot preparations, as for example, when injected in a properly selected pharmaceutically acceptable oil. The preferred oils are of vegetable origin such as sesame oil, cottonseed oil, corn oil, coconut oil, soybean oil, olive oil and the like, or they are synthetic esters of fatty acids and polyfunctional alcohols such as glycerol or propyleneglycol.

The depot compositions of the present invention are prepared by dissolving a highly lipophilic ester, amide or carbamate of the instant invention in a pharmaceutically acceptable oil under sterile conditions. The oil is selected so as to obtain a release of the active ingredient over a desired period of time. The appropriate oil may easily be determined by consulting the prior art, or without undue experimentation by one skilled in the art.

The dosage range at which the compounds of Formula I exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of Formula I will exhibit their therapeutic activities at dosages of between about 0.001 mg/kg of patient body weight/day to about 100 mg/kg of patient body weight/day.

The following examples are for illustrative purposes only and are not intended to limit the scope of the invention in any way.

EXAMPLE ONE

In Vivo Evidence Consistent with Voltage-Dependent Sodium Channel Blockade

Methods: The experimental procedure was based on the method of Bachauβ et al (1992). Male CD-1 mice weighing 35–40 g were anaesthetized with chloral hydrate (400 mg/kg). Under an operating microscope, a 3 mm vertical skin incision was made 2 mm behind the right orbit. The temporal muscle was deflected and a small craniotomy carried out to expose the dura. The dura was incised and deflected and the distal part of the right middle carotid artery exposed. The artery was occluded upstream to the main bifurcation by bipolar electroagulation with fine forceps. Infarct volume was measured 24 hours later using 2% triphenyltetrazolium chloride solution. In this experimental paradigm, HP 184 was orally administered to non-fasted mice (10 per group) one hour prior to occlusion. Infarct volume reduction was based on comparison to 1% acetic acid, vehicle, treated mice. Results are shown in Table 1.

TABLE 1

Neuroprotective activity of HP 184 in the mouse pMCAO stroke model

| Dose (mg/kg, po) | Time (min) | % infarct volume reduction mean sem |
|---|---|---|
| 1 | −60 | 21 ± 3 |
| 10 | −60 | 32 ± 11* |
| 10 | −60 | 40 ± 2.5** |

*$p < 0.05$;
**$p < 0.01$
The neuroprotection observed in a mouse permanent middle corotid artery occlusion model (pMCAO) is consistent with in vivo voltage-dependent sodium channel blockade at this dose and time.

EXAMPLE TWO

Effect of HP 184 On Edema After Photothrombotic Cerebral Lesion in the Rat

Rationale/Objective:

Thromboembolic stroke is the third cause of death in the western world. It is caused by a blood clot or disintegrating thrombus either being generated within the cerebral circulation or forming in the heart or large vessels and being carried into the cerebral circulation. Blood flow is then interrupted and an ischaemic lesion develops, with edema, necrosis and apoptosis of tissue. Edema is detrimental because it compresses the brain, promoting ischaemia, and also cell lysis and mechanical injury. Treatment with HP 184, a joint $Na^+/K^+$ channel blocker, was studied for its effects on this cerebral edema.

Method: Male Sprague Dawley rats (180–200 g bw) were anaesthetized with chloral hydrate (400 mg/kg ip) and placed in a stereotaxic apparatus. The skin was opened to reveal the skull and a cold light (Bioblock 150 W) was placed in contact with the right side of the skull forward of lambda. Bengal rose dye (10 mg/kg iv in saline) was administered intravenously and illumination of the skull started immediately and continued for 5 minutes. The skin was then sutured closed over the skull and the animal returned to its cage. Twenty-four hours after the photothrombotic lesion animals received HP184 made up in 1% tween in water by intravenous route at 0, 10 or 20 mg/kg body weight in a volume of 5 ml/kg. One hour later, animals were killed by decapitation and their brains removed (see appendix for protocol). Core samples were taken at the site of the lesion, and contralateral to the lesion, using a 6 mm diameter cork borer. Water content was determined by wet weight of tissue/dry weight of tissue and edema expressed as % excess water on lesioned sample compared with sample from contralateral hemisphere for each rat.

Results—Shown in Table 2

TABLE 2

| Treatment at 24 h post lesion | n | edema (% excess water) at 25 h post lesion |
| --- | --- | --- |
| vehicle | 26 | 4.10 ± 0.12 |
| HP 184 at 10 mg/kg iv | 12 | 3.61 ± 0.23 ns |
| HP 184 at 20 mg/kg iv | 13 | 3.20 ± 0.27 ** | stats: ANOVA plus Tukey-Kramer
**p < 0.001

HP 184 demonstrated a significant (22%) reduction of the edema in the right cerebral cortex one hour after iv administration at 20 mg/kg and 25 hours after photothrombotic lesion.

EXAMPLE THREE

Effect of HP184 On Lesion Size and Neurological Function After a Transient Focal Cerebral Ischemia in Rats Rationale/Objective:. In this study HP184 was administered 1 hour post-ischemia onset in a model of transient focal cerebral ischemia in rats. Parameters measured were lesion size and neurological function.

Methods: Male Sprague-Dawley rats [Iffa Credo, France] weighing about 220–240 g were anaesthetized with halothane (1.4%) in a nitrous oxide-oxygen mixture (70:30). Both common carotid arteries (CCAs) were isolated. The left middle cerebral artery (MCA) exposed via a temporal craniotomy was occluded with a microclip, and simultaneously the CCAs were occluded for 1 hour. Both body and cerebral temperatures were kept at normothermia. Following surgery animals were returned to their home cages in a room warmed at 24–26° C.

HP184, dissolved in 1% tween (in injectable sterile water), was administered at 10 and 20 mg/kg iv 1 hour after ischemia onset, and control rats received the vehicle according to the same protocol. At 24 h post-ischemia, a neurological function using a 9 points grading scale was performed blindly.

Grading Scale Used for the Neurological Function

| Item | Normal score | Deficit |
| --- | --- | --- |
| Placing reactions | | |
| Leg hanging  left forepaw | 1 | 0 |
| left | 1 | 0 |
| Visual | 1 | 0 |
| Grasping reflex  left forepaw | 1 | 0 |
| left | 1 | 0 |
| Righting reflex | | |
| head tilted  left side | 1 | 0 |
| right | 1 | 0 |
| Abnormal postures | Absent | Present |
| thorax twisting | 1 | 0 |
| left fore limb flexion | 1 | 0 |
| Global neurological score | 9 | |

Thereafter rats were killed and brains were removed. Fresh sections were cut with a brain matrix and stained with triphenyl tetrazolium chloride 2% at 37° C. for 5 min. The sections were then stored in 10% formalin at 4° C. for 24 h. Areas of infarction were measured with an image analyzer (Leica Q500).

Results: Ischemia induced the development of cerebral lesions in both the cortex and the striatum (See FIG. 1 which illustrates the effect of HP184 on brain damage at 10 and 20 mg/kg iv bolus 1 hour after MCA Occlusion). HP184 at 10 mg/kg iv significantly reduced the brain lesions by 41% (p<0.05). This reduction was significant in the cortex (−45%, p<0.05).

EXAMPLE FOUR

Measurement of Potassium Channel Blockade

Methods

PC12 cells (ATCC, Rockville, Md.) were grown in Dulbecco's modified Eagle's media supplemented with 10% fetal bovine serum (GIBCO BRL Grand Island, N.Y.).

Potassium channel currents were measured using standard patch clamp electrophysiolgy protocols as detailed previously (Rampe et al., 1998).

Results and Discussion

Potassium channel currents were elicited by 200 msec clamp pulses to +40 mV from a holding potential of −80 mV. This protocol resulted in a sustained outwardly directed current. Application of HP184 (10 μM) reduced the amplitude of this current and enhanced the rate of current decay. When current was measured at the end of the pulse, HP184 reduced current amplitude by 75±4% (n=4). The results are consisent with the notion that HP184 acts as an antagonist of voltage-dependent $K^+$ channels by blocking an activated state.

EXAMPLE FIVE

In Vivo Evidence of Enhancement Muscle Function

Objective: The inorganic dye ruthenium red (RuR) has been reported to block voltage-dependent $Ca^{+2}$ current in various cell types, including mouse sensory neurons (Duchen, 1992), synaptosomes and neuromuscular preparations (Hamilton and Lundy, 1995; Tapi and Velasco, 1997). Furthermore, RuR blocks release of neurotransmitters in brain synaptosomes (Meza-Ruiz and Tapia, 1978; Tapia and Meza-Ruiz, 1977) and neuromuscular junction (Alnaes and Rahamimoff, 1975; Person and Kuhn, 1979). In vivo, intraperitoneal (ip) administration of RuR causes flaccid paralysis in mice (Tapia et al, 1976) and this effect is antagonized by 4-aminopyridine (4-AP), a voltage-dependent $K^+$ channel blocker (Tapia, 1982). Tapia and Velasco (1997) have reviewed the effects of RuR both in vivo and in vitro, and suggest that RuR interacts with $Ca^{+2}$ sites located in the nerve ending membrane. Binding studies indicate that RuR selectively blocks N-type $Ca^{+2}$ channels, and these channels regulate the $Ca^{+2}$ influx necessary for neurotransmitter release. These authors also suggest that ip administration of RuR may be an experimental model of Eaton-Lambert myasthenic gravis syndrome, an autoimmune disease characterized by blockade of $Ca^{+2}$ entry and ACh release due to antibodies that bind to the N-type $Ca^{+2}$ channel. Consistent with this possibility, 4-AP has been reported to improve muscle weakness and restore neuromuscular transmission in patients (Lundh et al, 1977a; 1977b; 1979; McEvoy et al, 1989; Aisen et al, 1995).

The ability of both 4-aminopyridine (4-AP) and guanidine to antagonize RuR-induced flaccid paralysis is possibly due to their ability to facilitate neurotransmitter release (Lundh, 1978; Lundh and Thesleff, 1977; Tapia and Stiges, 1982). In any case, Tapia and coworkers (Tapia and Stiges, 1982) have reported that RuR blocks the release induced by 4-AP in synaptosomes.

In vitro, HP 184 enhances neurotransmitter release by a different mechanism than does 4-AP. At high concentrations, 4-AP enhances both electrically-stimulated and spontaneous release, but these effects are calcium dependent. In contrast, HP 184 enhances calcium-independent spontaneous neurotransmitter release only (Smith et al, 1993). It has also been hypothesized that spontaneous release has a functional role in vivo (Smith et al, 1996).

The purpose of the following experiment was to determine if HP 184 and 4-AP could antagonize the paralyzing effect of RuR after co-injection.

Method and Results: Groups of 4–5 mice (CD-1; Charles River; 25–35 grams) were separately but simultaneously injected ip with ruthenium red and vehicle (1% glacial acetic acid), ruthenium red and 4-AP, or ruthenium red and HP 184. The compound known as "8183" was also tested in this paradigm. Starting at 15 minutes after injections, mice were placed near a "flagpole" apparatus and their ability to support their own body weight (ie, to hold on to the flagpole and not fall) was recorded. Results were recorded as the number of mice that could support their own body weight versus the total number of mice tested. These results are shown in Table 3. All experiments were performed between 2 PM and 4:30 PM.

TABLE 3

| drug, dose | drug, dose | 15 min | 30 min | 45 min |
|---|---|---|---|---|
| RuR, 30 mg/kg ip | veh | 29 out of 69 (42%) | 19 out of 69 (27.5%) | 18 out of 64 (30.4%) |
| | 0.3 mg/kg 4-AP | 22 out of 25 (88%) | 13 out of 25 (52%) | 12 out of 25 (48%) |
| | 0.6 mg/kg 4-AP | 12 out of 14 (85.7%) | 8 out of 14 (57.1) | 8 out of 14 (57.1%) |
| | 30 mg/kg HP 184 | 15 out of 15 (100%) | 15 out of 15 (100%) | 15 out of 15 (100%) |
| | 10 mg/kg HP 184 | 14 out of 15 (93.3%) | 12 out of 15 (80%) | 11 out of 15 (73.3%) |
| | 30 mg/kg 8183 | 13 out of 14 (92.8%) | 13 out of 14 (92.8%) | 14 out of 14 (100%) |
| | 100 mg/kg DPH | 11 out of 20 (50%) | 10 out of 20 (50%) | 10 out of 20 (50%) |
| | 30 mg/kg DPH | 4 out of 15 (26.7%) | 3 out of 15 (20%) | 4 out of 15 (26.7%) |
| | 10 mg/kg RIL | 9 out of 15 (60%) | 4 out of 15 (26.7%) | 4 out of 15 (26.7%) |

Conclusion

Both 4-AP (ip) and HP 184 (ip) can antagonize the flaccid paralysis induced by the ip administration of RuR. This implies that HP 184 is able to enhance neuronal transmission in vivo, possibly via $K^+$ channel blockade. It is also possible, as it is for 4-AP, that HP 184 enhances neuronal transmission, since in vitro brain slice experiments support increased brain neurotransmitter release (Smith et al, 1993; 1996).

Doses of the sodium channel blockers diphenylhydaintoin (DPH) and riluzole (RIL) examined in this experimental paradigm were previously shown to be neuroprotective in focal ischemia models (Rataud et al, 1994; O'Neill et al, 1997). Their lack of effect in this model adds support to the interpretation that the ability of HP 184 to antagonize RuR-induced flaccid paralysis is probably not due to in vivo sodium channel blockade. This is clinically suggested as well. The negative symptoms of MS (loss of movement) are often worsened by sodium channel blockers (Sakurai and Kanazawa, 1999).

EXAMPLE SIX

Spinal Cord Crush Disease Models

Rationale and Objective: Gruner & Yee (1999) showed that, 25 days after spinal cord damage, 4-AP enhanced mMEP's following graded spinal cord injury in rats. Using identical procedures, functional behaviors were measured. These behaviors have been shown to correlate with minimal mMEP. The objective of these experiments was twofold:
1) to determine if HP 184 could attenuate spinal cord crush-induced motor impairments of moderate intensity if given acutely and to compare its effectiveness with methylprednisolone succinate (MPSS), and
2) to determine if HP 184 could improve motor function in rats with long-standing (25 days) spinal cord injury of minor intensity, and to compare its effect with 4-aminopyridine (4-AP).

Acute Treatment—i.p. Administration

Figure 2:
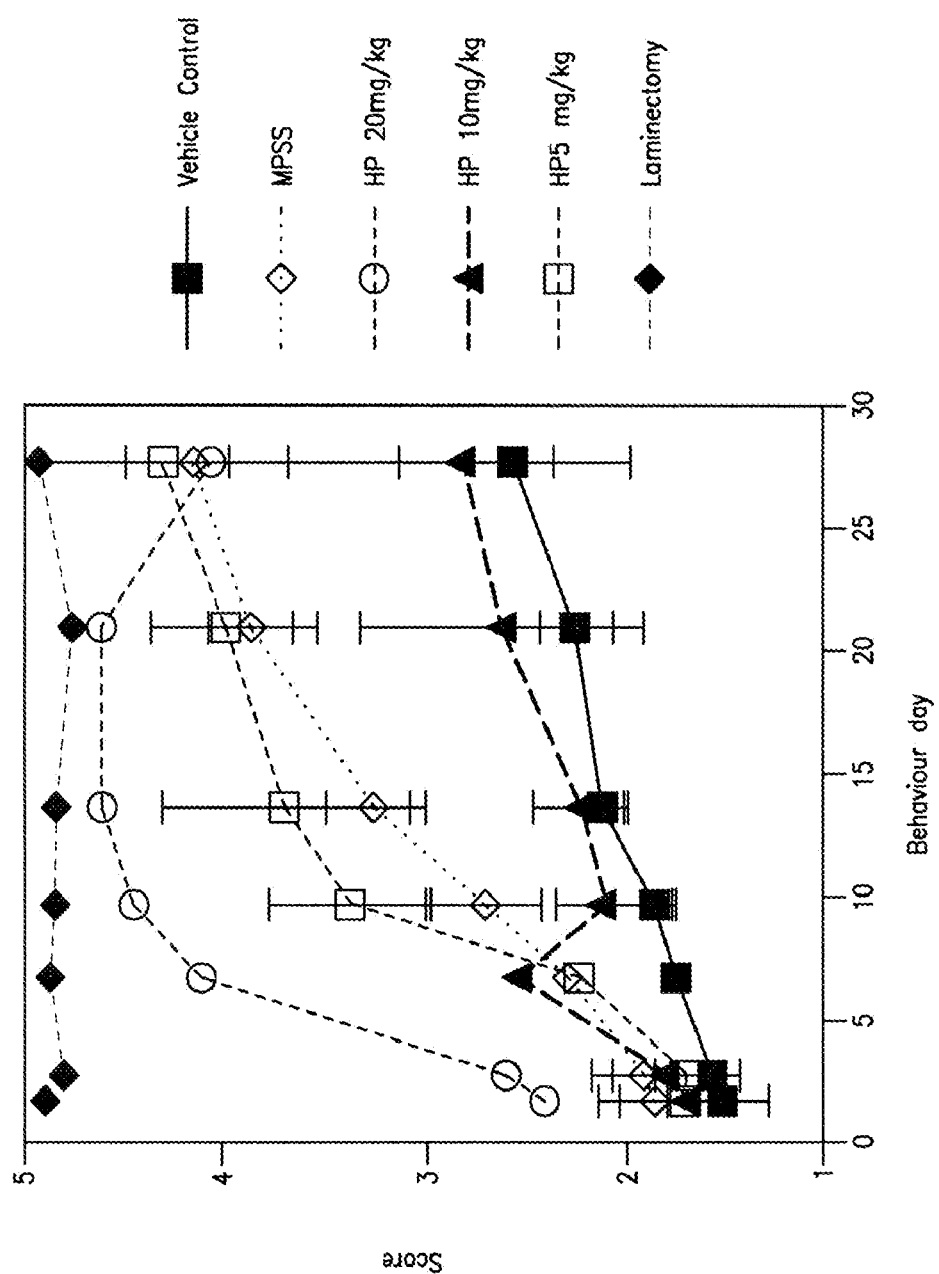
FIG. 2 shows the behavioral scores of rats after acute treatment with HP184 (ip administration) following spinal cord compression—(Example Six).

The spinal cords of female rats were exposed to laminectomy (sham, n=12) or crushed to a diameter of 1.4 mm (5 groups, n=12 each). Normal spinal cord diameter is approximately 2.5 mm. This compression represents a moderate injury characterized by initial open field walking scores of 1.5–2.5 in the Open Field Walking Scale. The definitions for the Open Field Walking Scale (OFT) are as follows:
0.0 No spontaneous movement
0.7 Slight movement
1.0 Movement in hip and/or knee (not ankle)
1.3 Active movement at hip and knee, not ankle
1.7 Questionable movement at ankle
2.0 Movement of the limb in all three major joints
2.3 Attempts at support
2.7 Support in stance only
3.0 Active support, uncoordinated gait
3.3 Intermittent bouts of coordinated gait
3.7 Lack of control of ankle or foot, walks on knuckles or on medial surface of the foot
4.0 Coordination of forelimbs and hindlimbs in gait
4.3 Improved hindlimb postural support, abdomen not low to ground
4.7 One or two toe drags, slight unsteadiness turning at full speed
5.0 Normal gait and base of support, no loss of balance on fast turns, no toe drags Drug Treatment Within 15 minutes of crush (day 1), rats in HP 184 designated groups received ip injections of 20, 10, 5 or 0 mg/kg in 1% glacial acetic acid vehicle. This administration was repeated on days 2 and 3. MPSS, on the other hand, was administered at 30 mg/kg ip at 15 minutes, 2 hours, 4 hours, and 6 hours on day 1 after crush. This MPSS dosing schedule has been described as optimal in the literature, and mirrors the dosing performed in humans. MPSS is currently the only drug therapy approved for human spinal cord injury. FIG. 2 shows the behavioral scores (OFT) of the various treatment groups over time. The normal preoperative score is 5. Rate and extent of improvement were significantly different from vehicle treated rats for both the 20 and 5 mg/kg dose groups. Each point represents the mean plus sem of 8–12 rats.

Acute Treatment—po Administration

Figure 3:
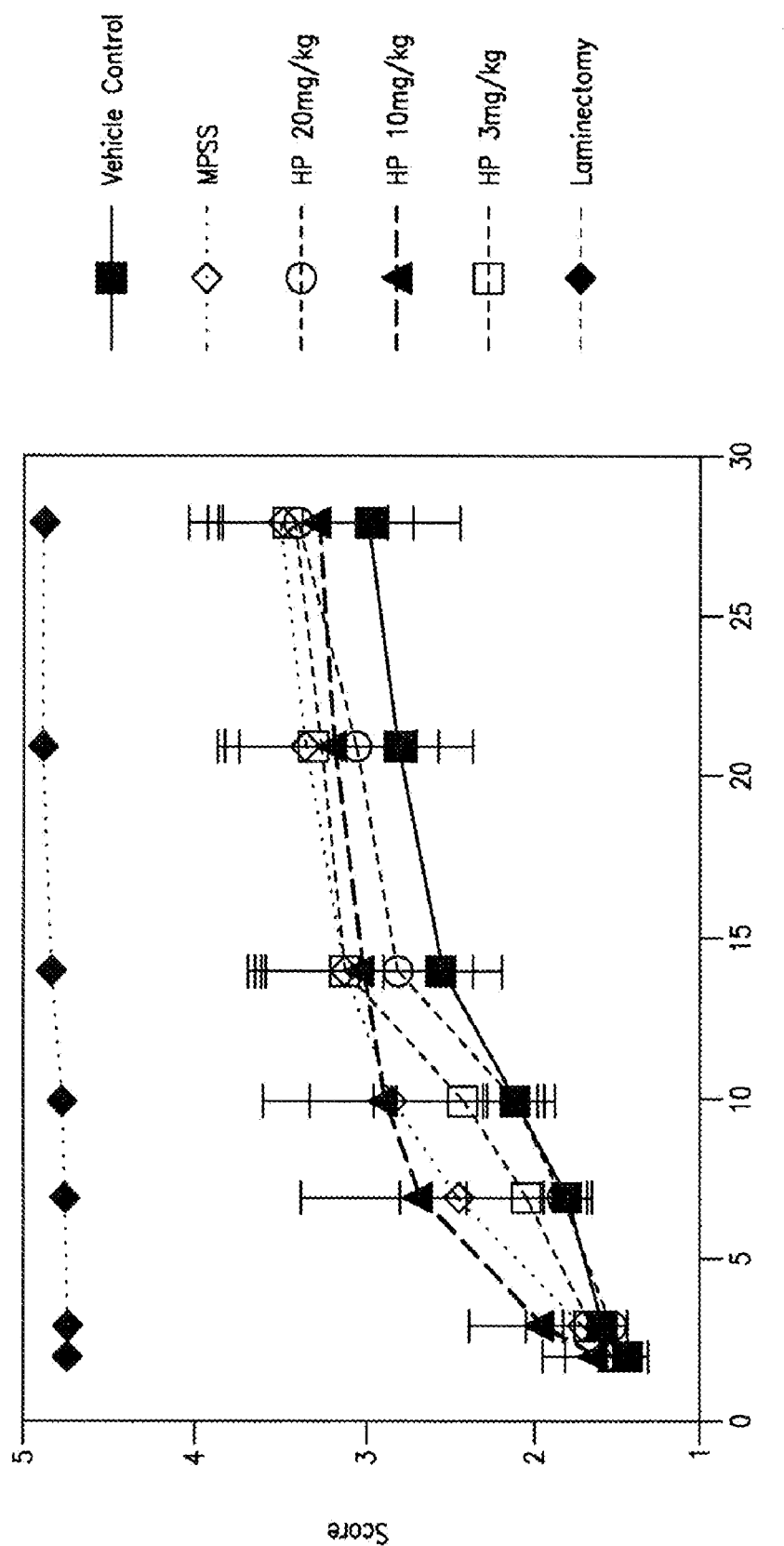
FIG. 3 shows the behavioral scores of rats after acute treatment with HP184 (po administration) following spinal cord compression—(Example Six).

Again, the spinal cords of female rats were exposed to laminectomy or crush to a diameter of 1.4 mm. In HP 184 groups, rats were orally treated 5–10 minutes prior to crush, and then once a day for days 2 and 3. MPSS was dosed as described before. Behavior scores (OFT) are shown in FIG. 3. The normal preoperative score is 5.

Rate and extent of improvement were improved for all doses, including the 10 mg/kg group, when compared to the vehicle treated group. Each point represents the mean plus sem of 12 rats.

Chronic Crush Experiment

Figure 4:
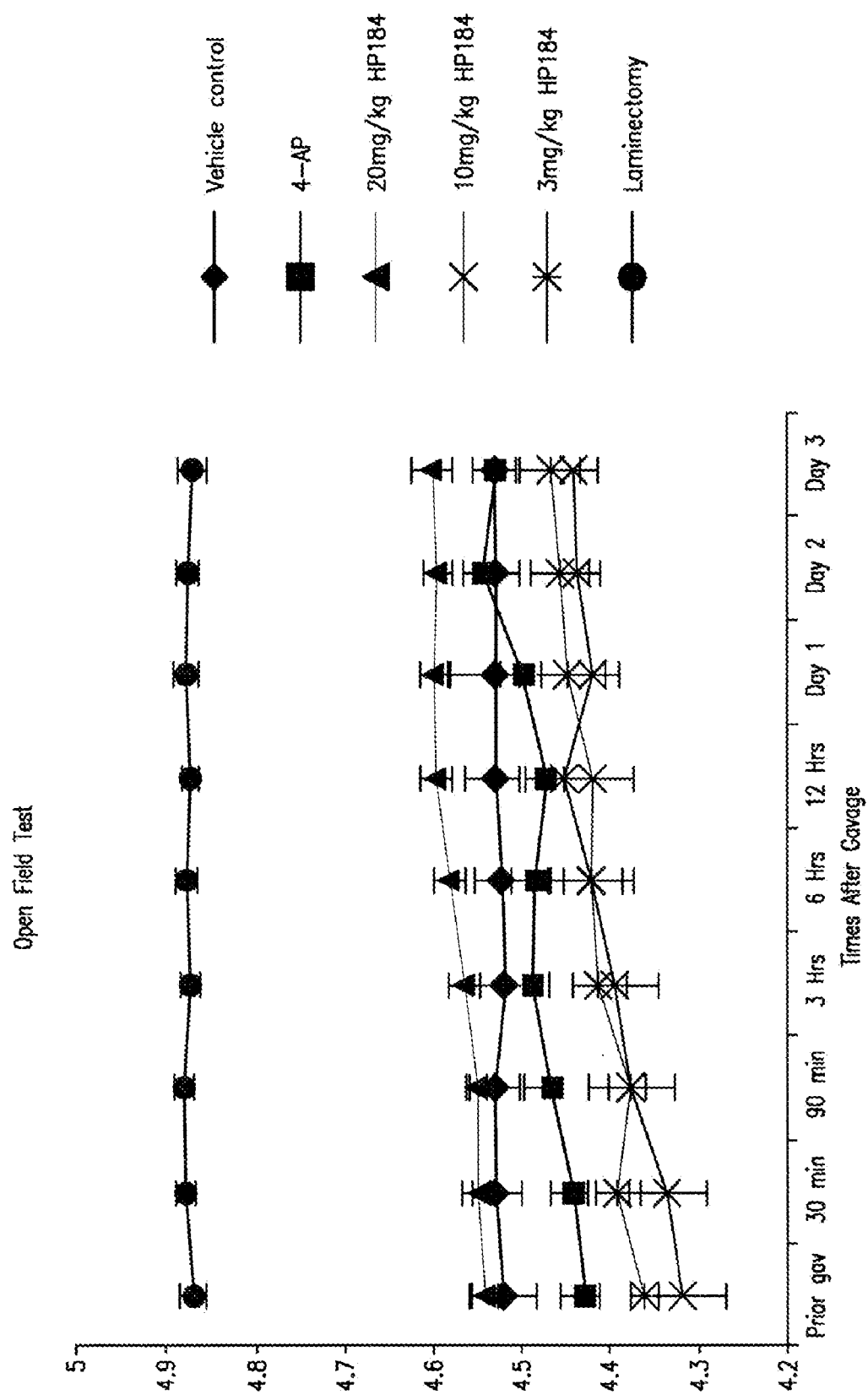
FIG. 4 shows the behavioral scores of rats in the Chronic Crush Experiment 25 days after a mild compression injury—(Example Six).

The spinal cords of female rats were exposed to laminectomy or crush to a diameter of 1.6 mm. This represented a minor injury, and was designed to result in OFT scores of 4.0 after 25 days of no treatment. This was chosen in an attempt to reproduce the same degree of motor impairment as described by Gruner and Yee (1999), who showed 4-AP induced improvements in hindlimb miniature endplate potential recordings. This procedure and length of untreated damage has also been shown to result in demyelination. Behavior scores (OFT) are shown in FIG. 4. FIG. 4 shows the means and standard errors of the groups using the Definitions for the Open Field Walking Scale described earlier herein.

In this experiment, OFT scores were slightly higher (4.3–4.5), leaving only a small window for improvement. Using each rat as its own control, consistent improvement was observed after once a day oral dosing of HP 184 on Day 26, 27 and 28. Consistent improvement was also observed after once a day ip 0.6 mg/kg 4-AP as well. The statistical differences were based upon the changes for each individual rat (each rat was its own control) using Mann-Whitney U-test. All the behavioral tests on day1, day2 and day3 were performed at 3 hours after gavage. There was no drug given on day 3 (first day started to give drug was day 0). The statistical analysis is as follows:

20 mg/kg—significant improvement at 3 h to day 3 (p=0.002) compared to vehicle control 10 mg/kg—significant improvement at 30 min and 3 h to 12 h (p=0.014) compared to vehicle control 3 mg/kg—significant improvement at 30 min to 6 h to day 1 (p=0.0027) compared to vehicle control 4-AP—significant improvement at 90 min to 3 h and 12 h to day 2 (p=0.0027) compared to vehicle control Table 4 illustrates the changes in scoring for each group from pre-dosing to three hours after the third consecutive daily dose.

TABLE 4

|  | Vehicle crush | 4-AP crush | 20 HP crush | 10 HP crush | 3 HP crush | Laminec No crush |
|---|---|---|---|---|---|---|
| Prior to dose | 4.52 ± 0.04 | 4.43 ± 0.03 | 4.54 ± 0.02 | 4.36 ± 0.01 | 4.32 ± 0.05 | 4.87 ± 0.01 |
| 3 hours after last dose | 4.53 ± 0.03 | 4.53 ± 0.02 | 4.60 ± 0.02 | 4.44 ± 0.03 | 4.47 ± 0.04 | 4.87 ± 0.01 |

Figure 5:
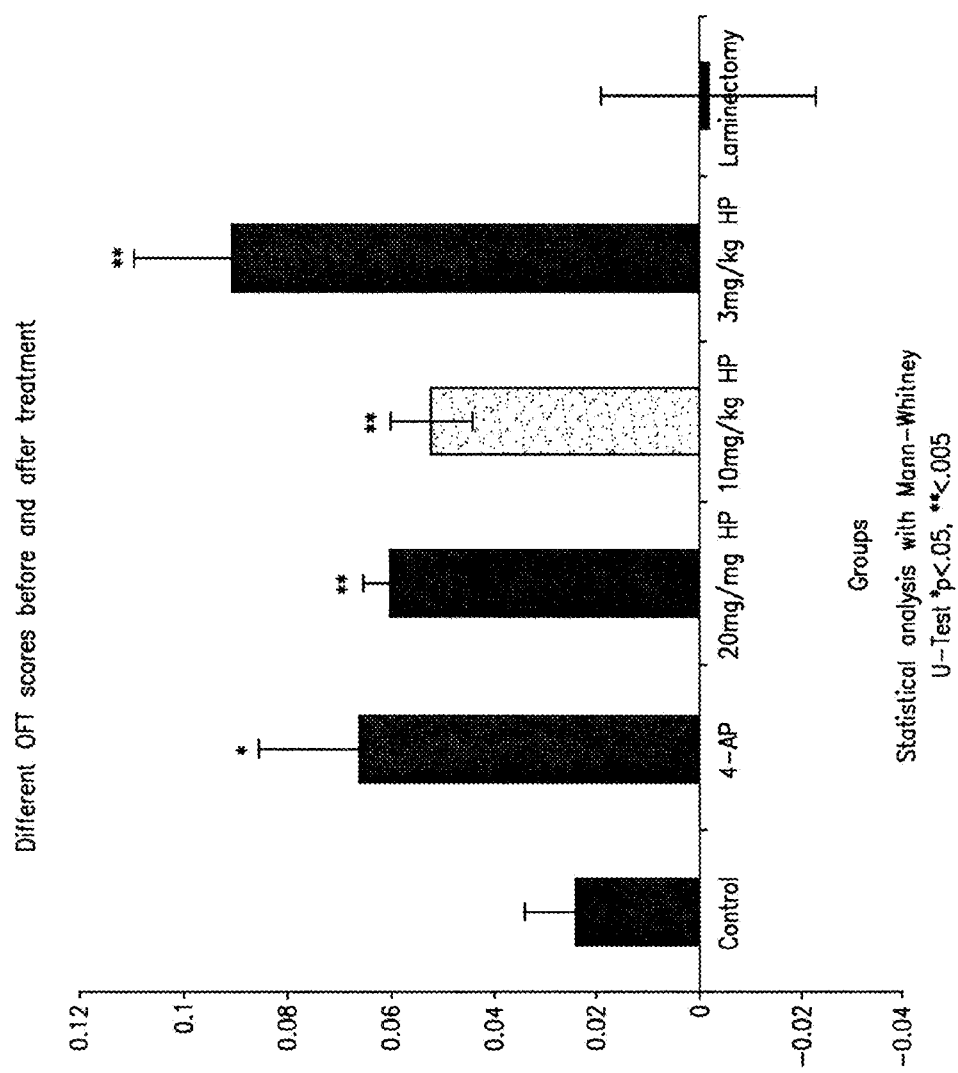
FIG. 5 shows the normalized difference in scoring for rats with a 25-day old mild compression injury—(Example Six).

FIG. 5 shows the changes in scoring, normalized for each rat. The graph shows the change observed after three consecutive days of dosing (from pre-dosing to three hours after the third consecutive daily dose) with either 0.6 mg/kg 4-AP (i.p.), 20 or 10 or 3 mg/kg (p.o.). Laminectomy refers to a sham group. The mean±sem for each group (n=12) is shown in FIG. 5.

Efficacy in Long Standing Spinal Cord Injury

Thirty-five days after a moderate degree of spinal cord injury, oral administration of 3 mg/kg HP 184 (po) improves motor recovery after a single dose, and daily dosing for 4 more days resulted in continued and sustained improvement based upon the definitions for the Open Field Walking Test described earlier herein. 4-AP, at 0.6 mg/kg (ip) was similarly effective. A tabular representation of the results from both chronic spinal cord injury studies (drugs first administered 25 days after a mild spinal cord crush and 35 days after a moderate spinal cord crush) are shown in Table 5.

TABLE 5

| Treatment | Day 25 (mild) prior | Day 28 (mild) 3 hrs after last dose | Delta | % possible improvement (highest score = 5) |
|---|---|---|---|---|
| Control | 4.52 ± .037 | 4.53 ± .026 | .01 | 2% |
| 4-AP (0.6 mpk, ip) | 4.43 ± .030 | 4.53 ± .023 | .10 | 17.5%* |
| HP 184 (3 mpk, po) | 4.32 ± .016 | 4.47 ± .035 | .15 | 22.0%* |

TABLE 5-continued

| Treatment | Day 35 (moderate) prior | Day 39 (moderate) 3 hrs after last dose | Delta | % possible improvement |
|---|---|---|---|---|
| Control | 4.00 ± .074 | 3.99 ± .057 | −.01 | −2% |
| 4-AP (0.6 mpk, ip) | 3.95 ± .084 | 4.17 ± .047 | .22 | 22.1%* |
| HP 184 (3 mpk, po) | 3.89 ± .054 | 4.17 ± .058 | .274 | 24.8%* |

As shown above, HP184 at 3 mg/kg/day by oral gavage from 35 to 41 days after moderate crush injury produced significant improvement. It was noted in this study that there was more myelin at the site of injury in the injured spinal cords of rats that received HP184. This data provides evidence consistent with the assertion that HP 184 is either enhancing remyelination or decreasing an ongoing demyelination process.

Further studies were carried out to determine the lowest effective dose of HP184 in the in the moderate chronic (35 days post-injury) crush paradigm in a double blind placebo and positively controlled design. The effects of HP184 previously observed at 3 mg/kg, po, were confirmed using 4AP (0.6 mg/kg, ip) as a positive control. Furthermore, the effect of all treatments on myelin staining was examined histologically.

(1) Behaviourial Assessment

One hundred fifty adult female Wistar rats, 250–300 g weight, obtained from Charles River were housed in the McMaster University Health Sciences Centre (HSC) Central Animal Facilities (CAF) for at least one week. During that time they were exposed to the performance tests described below, to ensure they were familiar with them. Rats were handled daily for 2 weeks prior to surgery.

Rats were anesthetized using isoflurane (3–5%): O2 (1L/min) in an appropriately equipped surgical suite in the CAF. Temgesic (0.03 mg/kg body weight, subcutaneously (SQ)) was administered prior to surgery for pain relief. Spinal cords were crushed (compressed) with a 3.5 mm wide modified coverslip forceps (Blight 1991, procedure revised by Rathbone laboratory). The forceps were closed to 1.4 mm for 15 sec, which produced injury level equivalent to the mid-level (moderate) outcome on the Gruner scale (1996). The compression injury was otherwise performed according to the procedure described by Blight (1991).

The animals were observed to determine pain behaviours, for presence of urinary tract infections or urinary retention. Pain was treated with Tynenol (0.8 mg/10 gm body weight orally).

To prevent the urinary infection, Septra (Trimethoprin-Sulfamethoxazole) was given orally (4.5 ml in 300 ml water) 1 day pre- and 5 days post-operation, and were treated with manual bladder expression. In the case of infections, i.e. any urinary tract infection, indicated by cloudy or bloody urine, Baytril (enrofloxacin, 7 mg/kg b.w.) was injected subcutaneously (SQ) twice a day.

Changes in locomotor behaviour and segmental reflexes were assessed up to 5 weeks post injury. Animals were tested in an open field walking task, hind limb placement and foot orientation. The animals were evaluated on days 2, 7, 14, 21, 28 and 35 after surgery. By 35 days after surgery, almost no further spontaneous recovery occurs. Therefore treatment began on day 35.

HP184 was dissolved in sterilized (autoclaved) deionized reverse-osmosis water acidified with glacial acetic acid (0.1 ml acid per 10 ml of water). 4-AP (Sigma, molecular weight 94.12; Jankowska E. et al., 1982; Gruner et al., 1999) was dissolved in physiological saline (0.6 mg/kg b.w.) and was administered by i.p. injection. One group of rats (vehicle control-1) received by oral gavage vehicle. Behaviourial testing was done immediately prior to receiving the gavage and at 3 hours thereafter. Then, the rats were scarified on day 35. All the other rats received either HP184 by oral gavage (0.3, 1, or 3 mg/kg bw depending on the group) or 4-AP (0.6 mg/kg, i.p.) or vehicle (vehicle control-2) once a day on the 35 to 42 days after surgery. On these days behaviourial tests were done immediately prior to receiving the gavage at 3 and 24 hours thereafter. Then, the rats were perfused on day 43 after the last behaviourial testing.

Video recording of the behaviourial testing using Hi-8, was done on days 35 to 43 after surgery.

Statistical analyses were performed on a Macintosh computer using GB-Stat ppc 6.5.2. The behavioral scores were analyzed by the Kruskal-Wallis nonparametric analysis of variance (ANOVA). Post hoc comparisons were made using Mann-Whitney U tests.

Figure 6A:
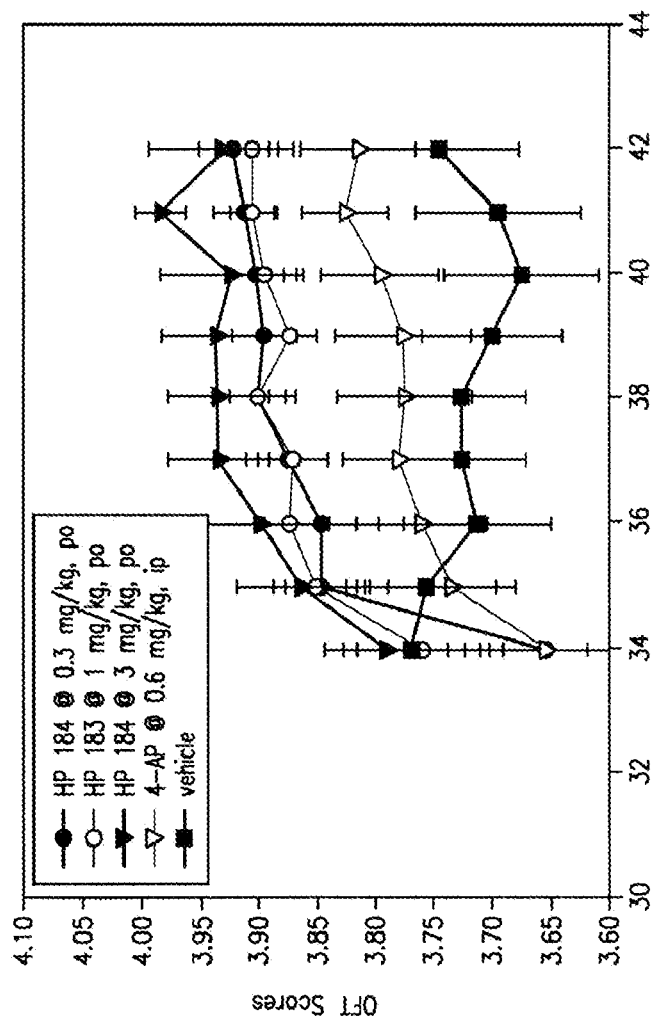
FIG. 6a shows open field locomotor ability assessment in animals with moderate compression injury—(Example Six).
Figure 6B:
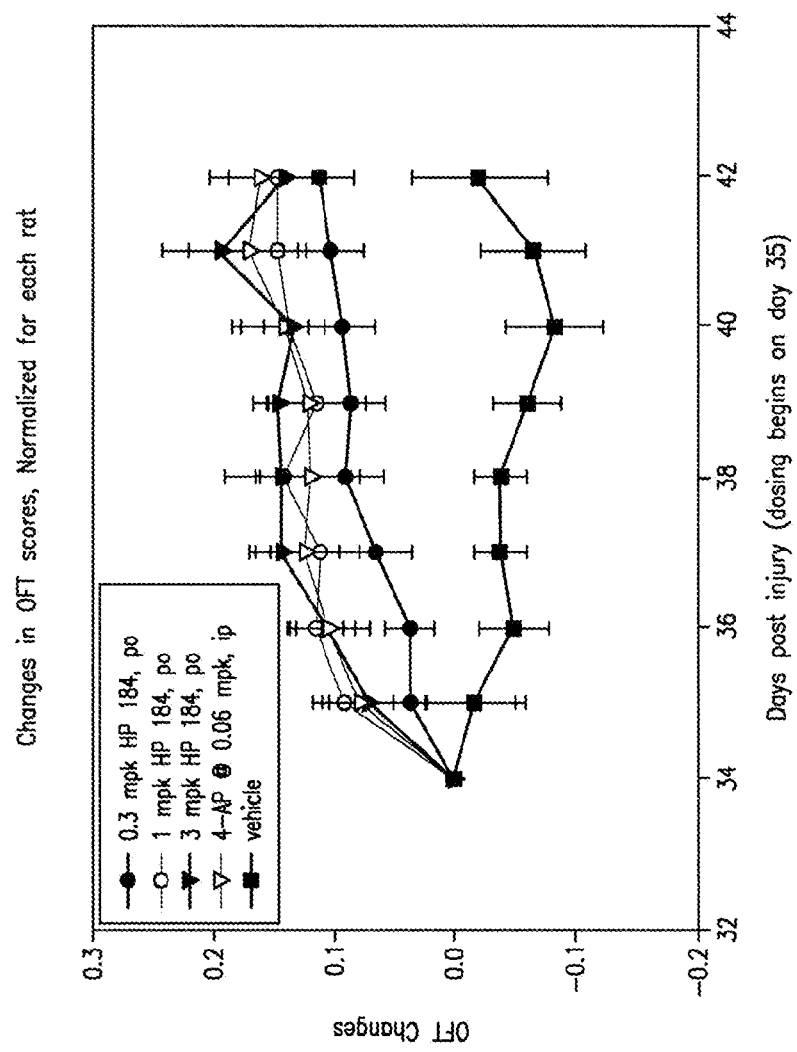
FIG. 6b shows open field locomotor ability assessment data in animals with moderate compression injury normalized for each rat—(Example Six).

The overview recovery of open field locomotor ability was assessed by the mean OFT scores for each groups, which are shown in FIGS. 6a and 6b. These results show that the performance of animals treated with HP184 or 4-AP was significantly different from that of control animals receiving vehicle. ANOVA for repeated measures shows treatment effect (p<0.01) on days 35–42.

The results show that both 4-AP and HP184 have beneficial effects, improving behavioral testing after moderate chronic spinal compression. Although all three concentrations of HP184 had beneficial effects, the 3 mg/kg of HP184 produced the best recovery of locomotor function thereby confirming the effects of HP184 observed previously at this dose. These results also indicate that the lowest (0.3 mg/kg) concentration of HP 184 may not be the lowest effective dose of HP184 in this paradigm.

Histological Study of Spinal Cords

A study to test whether the treatment with HP184 affected the amount of myelin in rats with moderate long term spinal cord crush injury when administered long after spinal cord injury.

The spinal cords from rats described above in the assessment were used for this study.

On postoperative day 21, the experimental subjects were deeply anesthetized with sodium pentobarbital (50–60 mg/kg body weight, i.p.) and perfused transcardically—first with 100 mL 0.05M phosphate buffed saline (PBS) containing 0.1% heparin, followed by 300–500 mL of 4% paraformaldehyde (PFA). Segments T9 to L1 of the spinal cords were taken out, then cryo-protected in 30% sucrose solution and frozen at −70° C. in 10.24% polyvinyl alcohol and 4.26% polyethylene glycol.

A segment of each cord including the lesion site plus 10 mm rostral and caudal to the lesion site was embedded in Tissue Tek medium. Serial sections were cut longitudinally at 20 μm intervals on a cryostat. Every third section was stained with luxol fast blue for myelin. The evaluation was performed by observers blinded as to treatment, on coded slides. Sections were examined under a light microscope for the extent of demyelination (the area without luxol fast blue staining).

For determinations of the maximal demyelinated area of the cord, the whole section was digitized on photographs using a Zeiss microscope. The extent of demyelination was measured at the lesion center using a computerized Bioquant BQ-TCW98 image analysis program by an investigator who was blind to treatment group.

Statistical analysis was performed on a Macintosh computer using GB-Stat ppc 6.5.2. The histological results were analyzed by the Kruskal-Wallis nonparametric analysis of variance (ANOVA). Post hoc comparisons were made using Mann-Whitney U tests.

Figure 7:
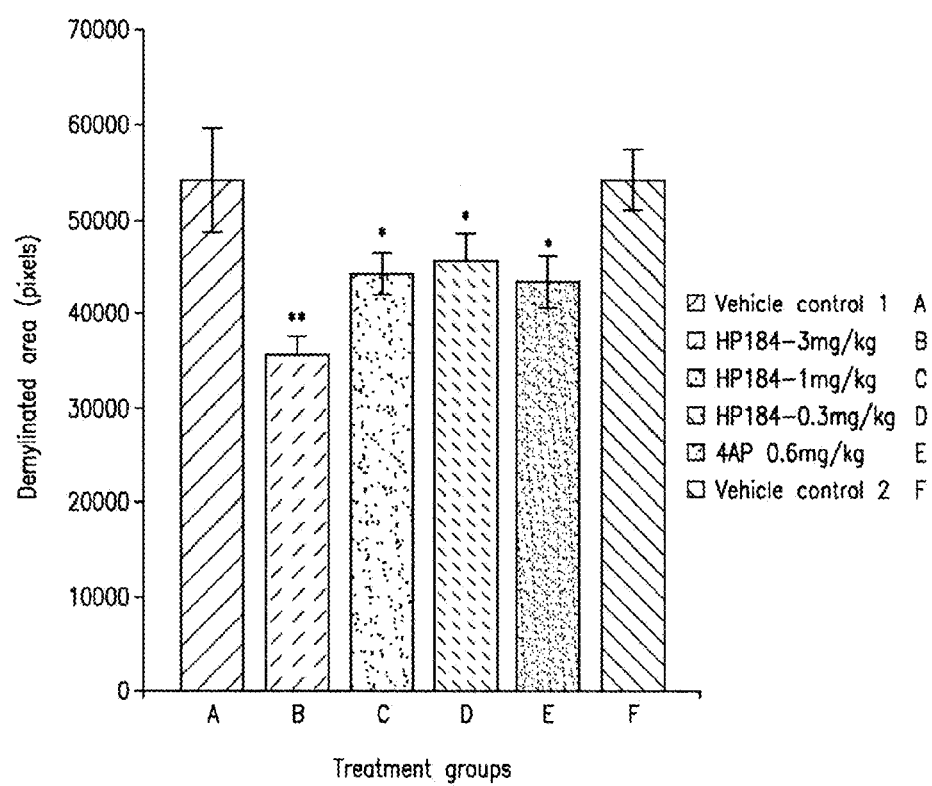
FIG. 7 shows effect of HP184 on demyelinated area at the moderate compression injury site—(Example Six).

The extent of demyelination for the six experimental groups (0.3, 1, or 3 mg/kg bw depending on the group or 4-AP 0.6 mg/kg or vehicle control 1 and 2) is shown in FIG. 7. The bars represent the number of pixels of demyelinated area at the crush center. (**$P<0.001$, *$P<0.05$, Kruskal-Wallis nonparametric analysis of variance (ANOVA)) The quantitative results show that the cords from HP184 or 4-AP treated animals had significantly greater myelinated area than that of saline controls. That is, the cords from animals which received vehicle injections had a significantly greater demyelinated area than that of either HP184 or 4-AP treated animals.

The histological analysis showed that both HP184 (at all three concentrations) and 4-AP have beneficial effects on myelination, which was consistent with the behavioral testing results. Of those groups, animals treated with 3 mg/kg of HP 184 showed the least demyelination. Therefore, 4-AP or HP184 appears capable of enhancing re-myelination at a stage long after spinal cord injury. It is improbable that the data simply represent a reduction in the rate of loss of myelin, since there was no difference in the extent of demyeliation in the two control groups, control 1 and control-2, evaluated at the beginning and end of the experiment.

EXAMPLE 7

The Effect of Intra Venous HP-184 on Bladder Irritation in the Rat

Figure 8:
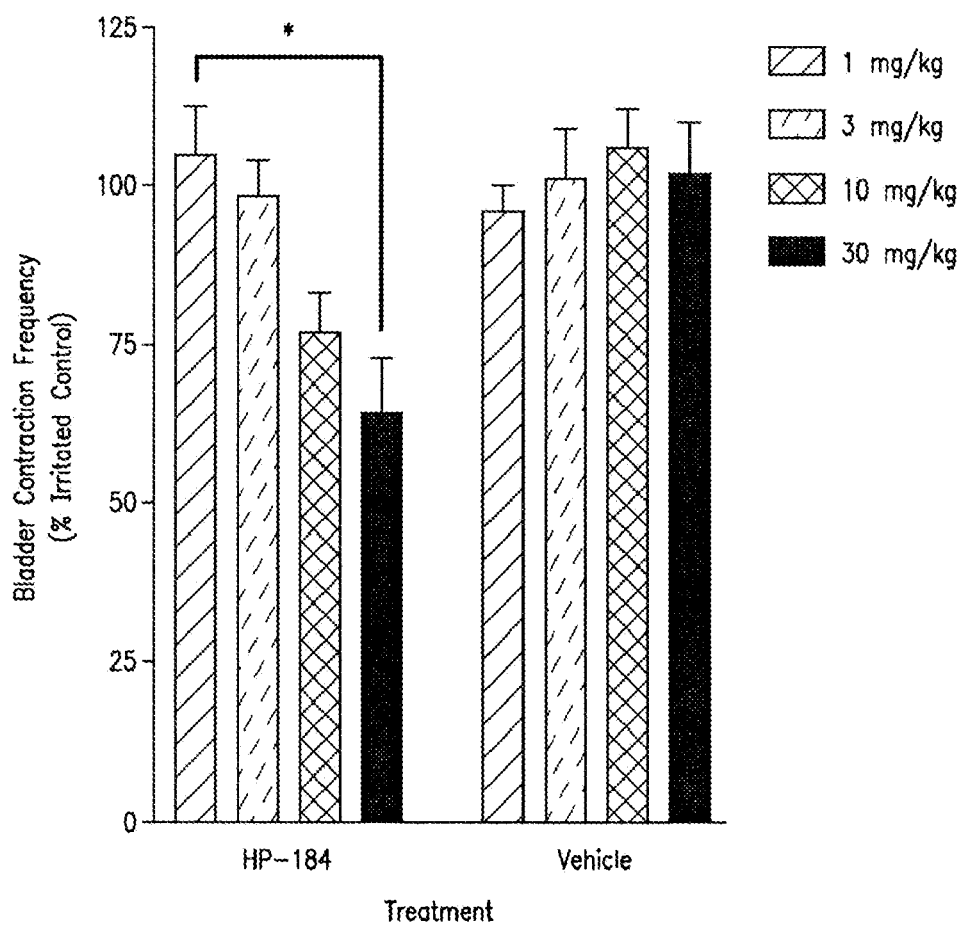
FIG. 8 shows the effects of HP184 on bladder contraction frequency—(Example 7).

This experiment shows the effect of intravenous HP184 in the KCl model outlined by Fraser et al (2001). Fraser et al combined protamine sulfate treatment, thought to breakdown urothelial umbrella cell barrier function, and physiologic urine concentrations of KCl (500 mM). The effects of intravenous HP-184 were compared to vehicle alone (n=4/group) in a cumulative dose-response study in urethane anesthetized rats with acute bladder irritation. Continuous open cystometry, which measures the filling and emptying of the bladder during continuous infusion, was utilized to determine the effect of the drug on bladder irritation. When the bladder is irritated, it contracts more frequently during the same filling rate due to sensitization of C-fiber afferent nerves. FIG. 8 illustrates the dose-dependent decrease in bladder contraction frequency from pre-administration irritation values compared to the effects of vehicle alone. Analysis of Variance for Repeated Measures indicates that while vehicle alone had no effect, HP-184 significantly decreased bladder contraction frequency in irritated bladders in a dose-dependent fashion ($P=0.001$ g).

EXAMPLE 8

The Effect of HP 184 on No Production in Mice

Figure 9:
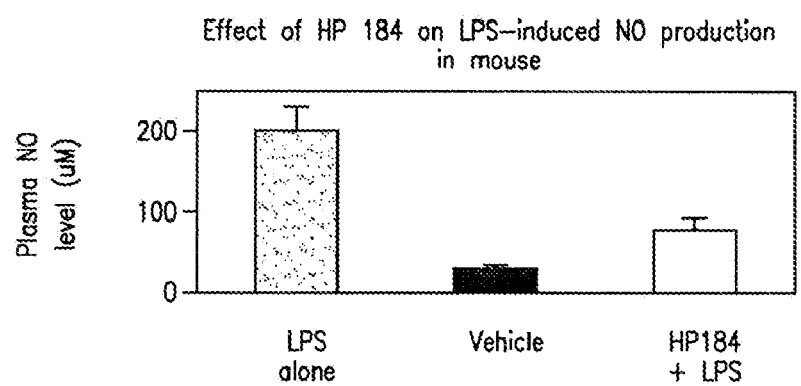
FIG. 9 shows the effect of HP184 on NO production in mice—(Example 8).

Mice were injected with 30 mg/kg HP 184 (ip) 30 minutes prior to LPS (3 mg/kg, ip). Mice were sacrificed 5 hours after LPS injection, and plasma collected. Nitrate levels were determined by the Griess assay. Groups were composed of 9–10 mice each. As shown graphically in FIG. 9, HP184 inhibits NO production. After one-way ANOVA, only LPS treatment was found to be significantly different ($p<0.01$) from vehicle treatment.

EXAMPLE 9

HP184 in a Neuropathic Pain Model

Figure 10:
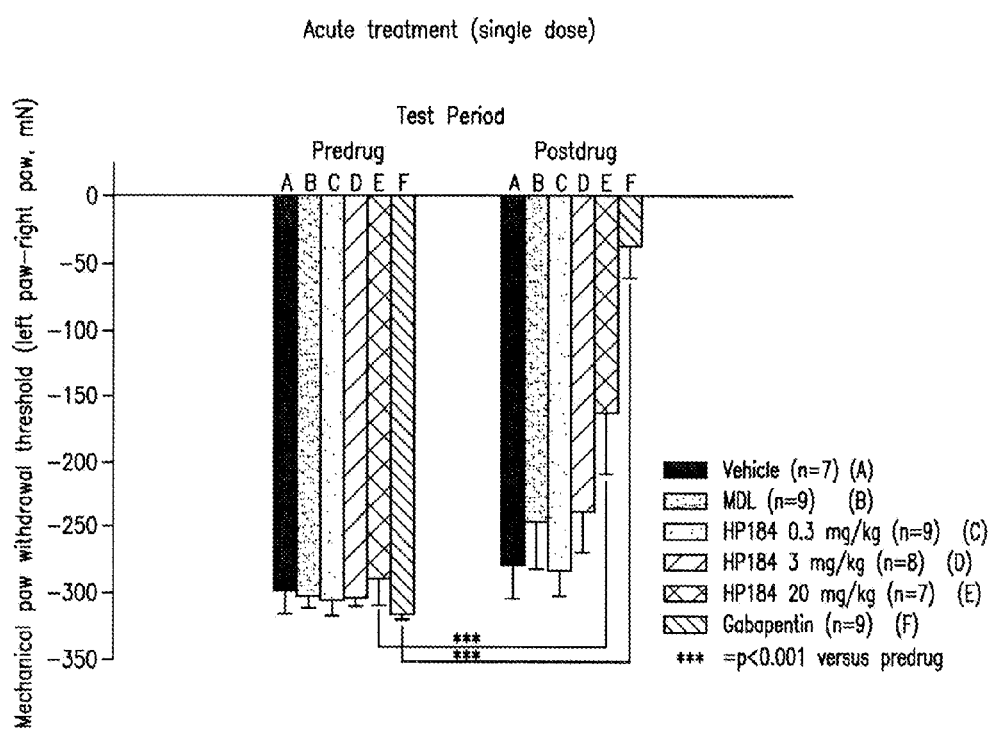
FIG. 10 shows the effect of HP184 in a neuropathic pain model—(Example 9).

Adult male Sprague-Dawley rats received unilateral constriction of the L6 nerve to produce chronic nerve injury. Following recovery from surgery (3–7 days post operative) animals were tested for paw withdrawal threshold to mechanical stimuli applied to the affected paw. This was determined by the application of calibrated von Frey monofilaments to the plantar surface of each hindpaw. Only animals with a 50% decrease in withdrawal threshold in the ligated paw were employed in the study, and were randomly assigned to one of 6 groups: three groups receiving one of three doses of HP 184 (0.3, 3 and 20 mg/kg, po), a fourth group receiving a single dose of another compound referred to MDL (10 mg/kg, ip), a fifth group receiving gabapentin (90 mg/kg, sc), and a sixth group receiving vehicle only. Behavioral testing occurred 45 minutes following the gabapentin (90 mg/kg, sc), and 3 hours following the HP 184, MDL, and vehicle. A difference score between the ligated and non-ligated paw withdrawal thresholds is calculated for each animal, and these differences were subjected to ANOVA with group as the main factor. The results are shown in FIG. 10. The graph shows the Mean (+/−SEM) difference of left (ligated) minus right (normal) paw withdrawal threshold before and after the first drug administration (acute phase of study). Statistical analysis reveals a dose-response attenuation of L5 ligation mechanical hyperlagesia by HP18420 mg/kg and a clear reversal of hyperalgesia by gabapentin 90 mg/kg. Analysis was between/within repeated measures ANOVA. This was followed by post-hoc comparison (LSD) on the group X time interaction term to exam pre versus post drug withdrawal threshold values.

Group: $F(5,43)=8.18$, $p<0.001$
Time: $F(1,43)=47.34$, $p<0.001$
Group X time: $F(5,43)=9.25$, $p<0.001$ In vehicle treated animals, there is a large difference in mechanical withdrawal thresholds between the two paws.

REFERENCES

Agoston S, Bowman W C, Houwertjes M C, Rodger I W, Savage A O. Direct action of 4-aminopyridine on the contractility of a fast-contracting muscle in the cat. Clin Exp Pharm Physiol 1982; 9: 21–34.

Aisen M L, Sevilla D, Gibson G, Kutt H, Blau A, Edelstein L, Hatch J and Blass J (1995) 3,4-Diaminopyridine as a treatment for amyotropic lateral sclerosis. J Neurol Sci. 129:21–24.

Alnaes E and Rahaminoff R (1975) On the role of mitochondria in transmitter release from motor nerve terminals. J. Physiol (Lond) 248:285–306.

Backhauβ C, Karkoutly C, Welsch M, and Krieglstein J (1992): A mouse model of focal cerebral ischemia for screening neuroprotective drug effects. J Pharmacological Meth. 27:27–32.

Ball A P, Hpokinson R B, Farrell I D (1979): Human botulism caused by *Clostridium Botulinum* type E: the Birmingham outbreak Q. J. Med. 48–473–491.

Behrmann D L, Bresnahan J C, Beattie M S, Shah B R. Spinal cord injury produced by consistent mechanical displacement of the cord in rats: behavioral and histologic analysis. J. Neurotrama, 9:197–217, 1992.

Bennett G J and Xie Y K (1998) A peripheral mononeuropathy in rat produces disorders of pain sensation like those seen in man. Pain. 33:87–107.

Bever C T (1996) Aminopyridines in Handbook of Multiple Sclerosis, ed SD Lick, Marcel Dekker, pp 429–42.

Bever C T, Jr., Young D, Anderson P A, Krumholz A, Conway K, Leslie J, Eddington N, Plaisance K I, Panitch H S, Dhib-Jalbut S. The effects of 4-aminopyridine in multiple sclerosis patients: results of a randomized, placebo-controlled, double-blind, concentration-controlled, crossover trial. Neurol 1994; 44:1054–1059.

Blight A R and DeCrescito V. Morphometric analysis of experimental spinal cord injury in the cat: the relation of injury intensity to survival of myelinated axons. Neuroscience 1986: 19:321–41.

Blight A R. Morphology of chronic spinal cord injury in the cat: Analysis of myelinated axons by line-samping. Neuroscience, 10:521–543, 1983.

Blight A R. Morphometric analysis of a model of spinal cord injury in guinea pigs, with behavioral evidence of delayed secondary pathology. J Neurol Sci, 103: 156–171, 1991.

Bostock H, Sherratt R M, Sears T A. Overcoming conduction failure in demyelinated nerve fibres by prolonging action potentials. Nature 1978; 274: 385–387.

Bostock H, Sears T A, Sherratt R M. The effects of 4-aminopyridine and tetraethylammonium ions on normal and demyelinated mammalian nerve fibres. J Physiol(Lond) 1981; 313: 301–315.

Bunge R P, Puckett W R, Bercerra J L, Marcillo A, Quencer R M. Observations on the pathology of human spinal cord injury. A review and classification of 22 new cases with details from a case of chronic cord compression with extensive focal demyelination. In: Seil F J, ed. Advances in neurology, vol 59, New York: Raven Press, 1993: 75–89.

Davis F A, Stefoski D, Rush J. Orally administered 4-aminopyridine improves clinical signs in multiple sclerosis. Ann Neurol 1990; 27: 186–192.

Duchen, M R (1992) Ca+2-dependent changes in the mitochondrial energetics in single dissociated mouse sensory neurons. Biochem J. 283:41–50.

Eder C (1998) Ion channels in microglia (brain macrophages) Am. J. Physiol. 275 (Cell Physiol. 44):C327–C342.

Fraser M O, Chuang Y, Lavelle J P, Yoshimura N, de Groat W C, Chancellor M B (2001) a reliable, nondestructive animal model for interstitial cystitus: intravesical low-dose protamine sulfate combine with physiological concentrations of potassium chloride. Urology 57(Suppl 1): 112

Gruner J A and Yee A K (1999) 4-Aminopyridine enhances motor evoked potentials following graded spinal cord compression injury in rats. Brain Res: 816:446–56.

Gruner J A, Wade C K, Menna G and Stokes B T. Myoelectric evoked potentials

Versus locomotor recovery in chronic spinal cord injured rats. J. neurotrauma, 10:327–347, 1993.

Gruner J A, Yee A K, Blight A R. Histological and functional evaluation of experimental spinal cord injury: evidence of a stepwise response to graded compression. Brain Res., 729:90–101, 1996.

Gruner J A, Yee A K. 4-Aminopyridine enhances motor evoked potentials following graded spinal cord compression injury in rats. Brain Res. January 23; 816(2):446–56, 1999.

Hamilton, M G and Lundy P M (1995) Effect of ruthenium red on voltage-sensitive Ca+2 channels. JPET 273:940–947.

Hayes K C, Blight A R, Potter P J, Allatt R D, Hsieh J T, Wolfe D L, Lam S, Hamilton J T. Preclinical trial of 4-aminopyridine in patients with chronic spinal cord injury. Paraplegia 1993; 31: 216–224.

Hayes K C, Potter P J, Wolfe D L, Hsieh J T, Delaney G A, Blight A R. 4-Aminopyridine-sensitive neurologic deficits in patients with spinal cord injury. J Neurotrauma 1994; 11: 433–446.

Hirsh J K, Quandt F N. Aminopyridine block of potassium channels in mouse neuroblastoma cells. J Pharmacol Exp Ther 1993; 267: 604–611.

Hockfield S. Carolson S, Evans C, et al. Selected methods for antibody and nuceic acid probes. USA: Cold Sprint Harbour Laboratory Press, p. 125–130, 1993.

Jankowska. E, Lundberg A., Rudomin P. and Sykova E. Effects of 4-Aminopyridine on synaptic transmission in the cat spinal cord. Brain Research, 240:117–129, 1982.

Jones R E, Heron J R, Foster D H, Snelgar R S, Mason R J. Effects of 4-aminopyridine in patients with multiple sclerosis. J Neurol Sci 1983; 60:353–362.

Kerasidis H, Wrathall J R and Gale K. Behavioral assessment of functional deficit in rats with contusive spinal cord injury. J. Neurosci. Methods, 20:167–179, 1987.

Lowry M A R, Goldbert J I and Belosevic M i(1998) Induction of nitric oxide (NO) synthesis in murine macrophages requires potassium channel activity. Clin Exp Immunol 111:597–603.

Lundh H (1978) Effects of 4-aminopyridine on neuromuscular transmission. Brain Res. 153:307–318.

Lundh H and Thesleff S (1977) The mode of action of 4-aminopyridine and guanidine on transmitter from motor nerve terminals. Eur. J. Pharmacol. 42:411–12.

Lundh H, Nilsson 0, Rosen I. 4-aminopyridine—a new drug tested in the treatment of Eaton-Lambert syndrome. J Neurol Neurosurg Psychiat 1977; 40: 1109–1112.

Lundh H, Leander S, Thesleff S (1977): Antagonism of the paralysis produced by botulinum toxin in the rat. J. Neurol. Sci. 32:29–43.

Kim S H ans Chung J M (1992) An experimental model for peripheral neuropathy produced by segmental spinal nerve ligation in the rat. Pain 50:355–363

Madge D J (1998): Sodium channels: recent developments and therapeutic potential, In Annual Reports in Medicinal Chemistry, Volume 33 (Bristol J A Editor in chief, Academic Press, San Diego), pp 51–60.

McEvoy K M, Windebank A J, Daube J R and Low P (1989): 3,4-Diaminopyridine in the treatment of Lambert-Eaton myasthenic syndrome (N. Engl. J. Med. 321:1567–71.

Mcllay L M, Halley F, Souness J E McKenna J, Benning V, Birrell M, Burton B, Belvisi M, Collis A, Constan A, Foster M, Hele D, Jayyosi Z, Kelley M, Maslen C, Miller G, Ouldelhkim M C, Page K, Phipps S, Pollock K, Porter B, Ratcliffe A J, Redford E J, Webber S, Slater B, Thybaud V, Wilsher N (2001) The discovery of RPR 200765A, a p38 MAP kinase inhibitor displaying a good oral anti-arthritic efficacy. Bioorg Med Chem 9:537–54.

Meza-Ruiz G and Tapia R (1978) [3H]GABA release in synaptosomal fractions after intracranial administration of ruthenium red. Brain Res. 154: 163–166.

O'Neill M J, Bath C P, Dell C P, Hicks C A, Gilmore J, Ambler S J, Ward M A, Bleakman D (1997): Effects of Ca2+ and Na+ channel inhibitors in vitro and in global cerebral ischaemia in vivo. *Eur J Pharmacol* 332(2): 121–31 RIL 10 mg/kg reference Pendlebury S T, Lee M A, Blamire A M, Styles P, and Matthews P M (2000) Correlating magnetic resonance imaging markers of axonal injury and demyelination in motor impairment secondary to stroke and multiple sclerosis. Magn. Reson. Imaging 18:369–78.

Person R J and Kuhn J A (1979) Depression of spontaneous and ionophore-induced transmitter release by ruthenium red at the neuromuscular junction. Brain Res. Bull 4:669–674.

Potter P J, Hayes K C, Hsieh J T, Delaney G A, Segal J L. Sustained improvements in neurological function in spinal cord injured patients treated with oral 4-aminopyridine: three cases. Spinal Cord 1998a; 36:147–155.

Potter P J, Hayes K C, Segal J L Hsieh J T, Brunnemann S R, Delaney G A, Tierney D S and Mason D (1998b): Randomized double-blind crossover trial of fampridine-SR (sustained release 4-aminopyridine) in patients with incomplete spinal cord injury. J. Neurotrauma 15:837–49.

Pyo H, Chung S, Jou I, Gwag B and Joe E H (1997) Expression and function of outward K+ channels induces by lipopolysaccharide in microglia. Mol Cells 7:610–614.

Qiao J, Hayes K C, Hsieh J T, Potter P J, and Delaney G A (1997): Effects of 4-aminopyridine on motor evoked potentials with spinal cord injury. J Neurotrauma 14:135–49.

Rampe, D., Murawsky, M. K., Grau, J. and Lewis, E. W. The antipsychotic agent sertindole is a high affinity antagonist of the human cardiac potassium channel HERG. J. Pharmacol. Exp. Ther. 286: 788–793, 1998.

Rataud J, Bebarnot F, Mary V, Pratt J and Stutzmann J M (1994): Comparative study of voltage-sensitive sodium channel blockers in focal ischaemia and electric convulsions in rodents. Neuro Sci Lett. 172:19–23.

Sakurai M and Kanazawa I (1999) Positive symptoms in multiple sclerosis: their treatment with sodium channel blockers, lidocain and mexiletine. J Neurol. Sci. 162: 162–168.

Saruhashi Y and Young W. Effect of mianserin on locomotory function after thoracic spinal cord hemisection in rats. Expl Neurol., 129:207–216, 1994

Savage A O. A comparison of the effects of 4-dimethylaminopyridine and 4-aminopyridine on isolated cardiac and skeletal muscle preparations. Arch Internat Pharmacodynam Therapie 1985; 273: 262–276.

Schwid S R, Petrie M D, McDermott MP, Tierney D S Mason D H and Goodman A D (1997): Quantitative assessment of sustained release 4-aminopyridine for symptomatic relief of multipule sclerosis. Neurology 48:817–21.

Segal J L, Pathak M S, Hernandez J P, Himber P L, Brunnemann S R and Charter R S (1999): Safety and efficacy of 4-aminopyridine in humans with spinal cord injury: A long-term, Controlled Trial. Pharmacotherapy 19:713–723.

Seltzer Z, Dubner R and Shir Y (1990) A novel behavioral model of neuropathic pain disorders produced in rats by partial sciatic nerve injury. Pain 43:205–218.

Sherratt R M, Bostock H, Sears T A. Effects of 4-aminopyridine on normal and demyelinated mammalian nerve fibres. Nature 1980; 283:570–572.

Shi R, Blight A R. Differential effects of low and high concentrations of 4-aminopyridine on axonal conduction in normal and injured spinal cord. Neurosci 1997; 77: 553–562.

Smith, C. P., A. T. Woods, Corbett, R., S. M. Chesson, G. M. Bores, W. W. Petko, J. E. Roehr and S. Kongsamut. Serotonergic activity of HP 184: Does spontaneous release have a role? Neurochemical Research 21:573–583, 1996.

Smith, C. P., L. R. Brougham, F. P. Huger, L. Davis, J. T. Klein and R. C. Effland. HP 184 [N-(n-propyl)-N-(3-fluroro-4-pyridinyl)-1H-3-methylindol-1-amine hydrochloride]: In vitro spontaneous release of acetylcholine (ACh) and norepinephrine (NE). Drug Dev. Res. 30:203–212, 1993.

Stefoski D, Davis F A, Faut M, Schauf C L. 4-Aminopyridine improves clinical signs in multiple sclerosis. Ann Neurol 1987; 21: 71–77.

Sweitzer S M, Colburn R W, Rutkowski M and DeLeo J A (1999) Acute peripheral inflammation induces moderate glial activation and spinal IL-1 expression that correlates with pain behavior in the rat. Brain Res. 829:209–221.

Tang L and Kongsamut S (1996) Frequency-dependent inhibition of neurotransmitter release by besipirdine and HP 184. Eur J Pharmacol 300:71–74.

Tang, L., Huger, F. P., Klein, J. T., Davis, L., Martin, L., Shimshock, S., Effland, R. C., Smith, C. P. and Kongsamut, S. (1998) 4-Aminopyridine derivatives: A family of novel modulators of voltage-dependent sodium-channels. Drug Dev. Res., 44:8–13.

Tang L., C. P. Smith and S. Kongsamut. Besipirdine inhibits effects of veratridine at the voltage dependent sodium channel. Br. J. Pharmacol 116:2468–2472, 1995.

Tapia R and Velasco I (1997) Ruthenium red as a tool to study calcium channels, neuronal death and the function of neural pathways. Neurochem Int 30: 137–147.

Tapia R and Meza-Ruiz G (1977) Inhibition by ruthenium red of the calcium-dependent release of [3H]GABA in synaptosomal fractions. Brain Res. 126: 160–166.

Tapia R, Meza-Ruiz G, Duran L and Drucker-Colin R D (1976) Convulsions or flaccid paralysis inued by ruthenium red depending on route of administration. Brain Res. 116:101–109.

Tapia R and Stiges M (1982) Effect of 4-aminopyridine on transmitter release in synaptosomes. Brain Res. 250: 291–9.

Tapia R (1982) Antagonism of the ruthenium red-induced paralysis in mice by 4-aminopyridine, guanidine and lanthanum. Neurosci Lett 35:615–623.

Targ E F, Kocsis J D. 4-Aminopyridine leads to restoration of conduction in demyelinated rat sciatic nerve. Brain Res 1985; 328: 358–361.

Targ E F, Kocsis J D. Action potential characteristics of demyelinated rat sciatic nerve following application of 4-aminopyridine. Brain Res 1986; 363: 1–9.

van Diemen H A, Polman C H, van Dongen T M, van Loenen A C, Nauta J J, van Walbeek H K, Koetsier J C. The effect of 4-aminopyridine on clinical signs in multiple sclerosis: a randomized, placebo-controlled, double-blind, cross-over study. Ann Neurol 1992; 32: 123–130.

van Diemen H A, Polman C H, van Dongen M M, Nauta J J, Strijers R L, van Loenen A C, Bertelsmann F W, Koetsier J C. 4-Aminopyridine induces functional improvement in multiple sclerosis patients: a neurophysiological study. J Neurol Sci 1993; 116: 220–226.

Yamaguchi S and Rogawski M A (1992): Effects of anticonvulsant drugs on 4-aminopyridine-induced seizures in mice. Epilepsy Res. 11:9–16.

Patents:

Effland R C, Klein J T, Davis K L Olsen G E; U.S. Pat. No. 4,970,218 entitled "N-(Pyridinyl)-1H-indol-1-amines".

Hansebout R R and Blight A R; U.S. Pat. No. 5,545,648 entitled "Use of 4-aminopyrdidine in the reduction of chronic pain and spasticity in a spinal cord injured patient".

Hansebout R R and Blight A R; WO 94/14439 entitled "The use of 4-aminopyridine in the treatment of a neurological condition".

Huger, F. P., Kongsamut, S., C. P. Smith & L. Tang. U.S. Pat. No. 5,776,955 entitled "Use of unsubstituted and substituted N-(pyrrol-1-yl) pyridinamines as anticonvulsant agents".

Kongsamut, S., C. P. Smith & A. T. Woods; U.S. Pat. No. 5,356,910 entitled "Use of N-(Pyridinyl)-1H-indol-1-amines for the Treatment of Obsessive Compulsive Disorder".

Kongsamut, S., C. P. Smith & A. T. Woods; U.S. Pat. No. 5,356,910 entitled "Use of N-(Pyridinyl)-1H-indol-1-amines for the preparation of a medicament for the treatment of obsessive-compulsive disorders".

Masterson J G and Myers M; U.S. Pat. No. 5,370,879 entitled "Formulations and their use in the treatment of neurological diseases".

Masterson J G and Myers M; U.S. Pat. No. 5,580,580 entitled "Formulations and their use in the treatment of neurological diseases".

Masterson J G and Myers M; U.S. Pat. No. 5,540,938 entitled "Formulations and their use in the treatment of neurological diseases".

Wurtman R J and Buyukysal R; WO 89/09600 entitled "Method and composition for treating neurological disorders".

The invention claimed is:

1. A method of treating Over Active Bladder said method comprising administering to a patient in need thereof a therapeutically effective amount of a compound of formula I

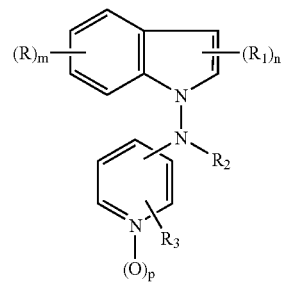

wherein
m is 0, 1 or 2;
n is 0, 1 or 2;
p is 0 or 1;
each R is independently hydrogen, halogen, trifluoromethyl, $C_1$–$C_6$alkyl, $C_1$–$C_6$alkoxy, benzyloxy, hydroxy, nitro or amino;
each $R_1$ is independently hydrogen, $C_1$–$C_6$alkyl, $C_1$–$C_6$alkenyl, $C_1$–$C_6$alkanoyl, halogen, cyano, —C(O)$C_1$–$C_6$alkyl, —$C_1$–$C_6$alkyleneCN, —$C_1$–$C_6$alkyleneNR'R" wherein R' and R" are each independently hydrogen or $C_1$–$C_6$alkyl, —$C_1$–$C_6$alkyleneOC(O)$C_1$–$C_6$alkyl, or —CH(OH)$R_4$ wherein $R_4$ is hydrogen or $C_1$–$C_6$alkyl;
$R_2$ is hydrogen, $C_1$–$C_6$alkyl optionally substituted with halogen, hydroxy or benzyloxy, $C_1$–$C_6$alkenyl, $C_1$–$C_6$alkynyl, —CO$_2$$C_1$–$C_6$alkyl, or —$R_5$—NR' R" wherein $R_5$ is $C_1$–$C_6$alkylene, $C_1$–$C_6$alkenylene or $C_1$–$C_6$alkynylene and R' and R" are each independently hydrogen, $C_1$–$C_6$alkyl or alternatively the group —NR'R" as a whole is 1-pyrrolidinyl; and
$R_3$ is hydrogen, nitro, amino, halogen, $C_1$–$C_6$alkoxy, hydroxy or $C_1$–$C_6$alkyl
or a pharmaceutically acceptable salt thereof.

2. The method of claim 1 wherein the compound has the following formula:

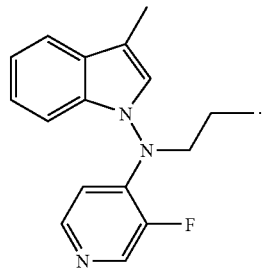

* * * * *